(12) United States Patent
Matityahu

(10) Patent No.: US 9,072,548 B2
(45) Date of Patent: Jul. 7, 2015

(54) SPINE REPAIR ASSEMBLY

(75) Inventor: Amir M. Matityahu, Los Altos, CA (US)

(73) Assignee: Anthem Orthopaedics LLC, Los Altos, CA (US)

( * ) Notice: Subject to any disclaimer, the term of this patent is extended or adjusted under 35 U.S.C. 154(b) by 374 days.

(21) Appl. No.: 11/759,429

(22) Filed: Jun. 7, 2007

(65) Prior Publication Data

US 2008/0306550 A1    Dec. 11, 2008

(51) Int. Cl.

| | |
|---|---|
| A61B 17/70 | (2006.01) |
| A61B 17/58 | (2006.01) |
| A61B 17/80 | (2006.01) |
| A61B 17/17 | (2006.01) |
| A61B 17/86 | (2006.01) |
| A61B 17/88 | (2006.01) |

(52) U.S. Cl.
CPC ............ *A61B 17/7059* (2013.01); *A61B 17/80* (2013.01); *A61B 17/8061* (2013.01); *A61B 17/8052* (2013.01); *A61B 17/1728* (2013.01); *A61B 17/1757* (2013.01); *A61B 17/8023* (2013.01); *A61B 17/8047* (2013.01); *A61B 17/8057* (2013.01); *A61B 17/863* (2013.01); *A61B 17/8635* (2013.01); *A61B 17/8875* (2013.01)

(58) Field of Classification Search
USPC .............. 606/70, 71, 280, 902, 248, 290, 291
See application file for complete search history.

(56) References Cited

U.S. PATENT DOCUMENTS

| | | | |
|---|---|---|---|
| 2,267,925 A | 2/1941 | Johnston | |
| 2,699,774 A | 1/1955 | Livingston | |
| 3,255,747 A | 6/1966 | Cochran et al. | |
| 3,463,148 A | 8/1969 | Treace | |
| 4,219,015 A | 8/1980 | Steinemann | |
| 4,297,993 A | 11/1981 | Harle | |
| 4,484,570 A | 11/1984 | Sutter et al. | |

(Continued)

FOREIGN PATENT DOCUMENTS

| | | |
|---|---|---|
| DE | 10131992 B4 | 11/2006 |
| FR | 2861980 | 5/2005 |

(Continued)

OTHER PUBLICATIONS

Filed Response to Oct. 19, 2011 Official Action issued by the Australian Patent Office for AU patent application serial No. 2006306120, Oct. 15, 2012, also pp. 1-28.

(Continued)

*Primary Examiner* — Christian Sevilla
(74) *Attorney, Agent, or Firm* — Intellectual Innovations Legal Advisors

(57) ABSTRACT

A spine repair system and assembly are disclosed. The spine repair system includes a plate for use with a plurality of bone screws to treat a mammalian body having a plurality of vertebral portions in a spine. The plate has an elongate plate-like member having first and second end portions adapted for fastening respectively to a plurality of vertebral portions. First and second end portions are provided with a plurality of apertures for receipt of bone screws, including one or more apertures inclined relative to the plate-like member so as to enhance securement of the first and second end portions to the first and second vertebral portions when the bone screws are introduced through the screw holes into the vertebral portions. A method of operation and use are also disclosed.

20 Claims, 16 Drawing Sheets

(56) References Cited

U.S. PATENT DOCUMENTS

| | | | |
|---|---|---|---|
| 4,488,543 A * | 12/1984 | Tornier | 606/65 |
| 5,057,111 A | 10/1991 | Park | |
| 5,108,399 A | 4/1992 | Eitenmuller et al. | |
| 5,127,914 A * | 7/1992 | Calderale et al. | 606/65 |
| 5,147,361 A * | 9/1992 | Ojima et al. | 606/70 |
| 5,190,544 A | 3/1993 | Chapman et al. | |
| 5,329,959 A | 7/1994 | Owen et al. | |
| 5,364,399 A * | 11/1994 | Lowery et al. | 606/295 |
| 5,470,333 A * | 11/1995 | Ray | 606/261 |
| 5,487,377 A * | 1/1996 | Smith et al. | 600/204 |
| 5,527,311 A * | 6/1996 | Procter et al. | 606/280 |
| 5,545,164 A * | 8/1996 | Howland | 606/250 |
| 5,545,165 A | 8/1996 | Biedermann et al. | |
| 5,549,612 A * | 8/1996 | Yapp et al. | 606/293 |
| 5,601,553 A * | 2/1997 | Trebing et al. | 606/86 B |
| 5,603,713 A | 2/1997 | Aust et al. | |
| 5,616,144 A | 4/1997 | Yapp et al. | |
| 5,690,631 A * | 11/1997 | Duncan et al. | 606/281 |
| 5,735,853 A | 4/1998 | Olerud | |
| 5,766,175 A * | 6/1998 | Martinotti | 606/285 |
| 5,800,433 A * | 9/1998 | Benzel et al. | 606/250 |
| 5,897,557 A | 4/1999 | Chin et al. | |
| 5,954,722 A * | 9/1999 | Bono | 606/281 |
| 6,129,730 A * | 10/2000 | Bono et al. | 606/291 |
| 6,139,550 A * | 10/2000 | Michelson | 606/70 |
| 6,214,012 B1 | 4/2001 | Karpman et al. | |
| 6,235,033 B1 | 5/2001 | Brace et al. | |
| 6,293,949 B1 | 9/2001 | Justis et al. | |
| 6,331,179 B1 | 12/2001 | Freid et al. | |
| 6,342,055 B1 | 1/2002 | Eisermann et al. | |
| 6,402,756 B1 * | 6/2002 | Ralph et al. | 606/71 |
| 6,544,266 B1 | 4/2003 | Roger et al. | |
| 6,575,975 B2 | 6/2003 | Brace et al. | |
| 6,592,586 B1 * | 7/2003 | Michelson | 606/71 |
| 6,663,632 B1 | 12/2003 | Frigg | |
| 6,740,088 B1 * | 5/2004 | Kozak et al. | 606/286 |
| 6,783,382 B2 * | 8/2004 | Felps | 439/314 |
| 6,786,909 B1 | 9/2004 | Dransfeld et al. | |
| 6,890,334 B2 | 5/2005 | Brace et al. | |
| 6,893,443 B2 | 5/2005 | Frigg et al. | |
| 6,908,466 B1 | 6/2005 | Bonutti et al. | |
| 6,916,321 B2 | 7/2005 | TenHuisen et al. | |
| 6,916,483 B2 | 7/2005 | Ralph et al. | |
| 7,195,633 B2 | 3/2007 | Medoff et al. | |
| 7,220,263 B2 | 5/2007 | Cordaro | |
| 7,547,305 B2 * | 6/2009 | Rapp | 606/70 |
| 7,682,379 B2 | 3/2010 | Mathieu et al. | |
| 7,846,163 B2 | 12/2010 | Fourcault et al. | |
| 2002/0045896 A1 * | 4/2002 | Michelson | 606/61 |
| 2002/0045897 A1 * | 4/2002 | Dixon et al. | 606/61 |
| 2002/0058939 A1 | 5/2002 | Wagner et al. | |
| 2002/0065517 A1 * | 5/2002 | Paul | 606/69 |
| 2002/0077630 A1 | 6/2002 | Lin | |
| 2002/0111630 A1 * | 8/2002 | Ralph et al. | 606/71 |
| 2002/0120271 A1 * | 8/2002 | Dixon et al. | 606/61 |
| 2002/0156474 A1 | 10/2002 | Wack et al. | |
| 2003/0074001 A1 * | 4/2003 | Apfelbaum et al. | 606/71 |
| 2003/0105461 A1 | 6/2003 | Putnam | |
| 2003/0105471 A1 | 6/2003 | Schlapfer et al. | |
| 2003/0199876 A1 | 10/2003 | Brace et al. | |
| 2004/0013703 A1 | 1/2004 | Ralph et al. | |
| 2004/0015169 A1 | 1/2004 | Gause | |
| 2004/0030339 A1 | 2/2004 | Wack et al. | |
| 2004/0039387 A1 * | 2/2004 | Gause et al. | 606/69 |
| 2004/0059335 A1 | 3/2004 | Weaver et al. | |
| 2004/0068319 A1 | 4/2004 | Cordaro | |
| 2004/0116931 A1 * | 6/2004 | Carlson | 606/70 |
| 2004/0127896 A1 | 7/2004 | Lombardo et al. | |
| 2004/0127904 A1 | 7/2004 | Konieczynski et al. | |
| 2004/0158250 A1 * | 8/2004 | Chappuis | 606/69 |
| 2004/0167522 A1 | 8/2004 | Niederberger et al. | |
| 2004/0181228 A1 | 9/2004 | Wagner et al. | |
| 2004/0204712 A1 | 10/2004 | Kolb et al. | |
| 2004/0204713 A1 * | 10/2004 | Abdou | 606/71 |
| 2004/0220570 A1 | 11/2004 | Frigg | |
| 2004/0236332 A1 | 11/2004 | Frigg | |
| 2004/0254579 A1 | 12/2004 | Buhren et al. | |
| 2004/0260291 A1 * | 12/2004 | Jensen | 606/69 |
| 2005/0010226 A1 * | 1/2005 | Grady et al. | 606/69 |
| 2005/0015131 A1 | 1/2005 | Fourcault et al. | |
| 2005/0043736 A1 * | 2/2005 | Mathieu et al. | 606/73 |
| 2005/0049594 A1 * | 3/2005 | Wack et al. | 606/69 |
| 2005/0070904 A1 | 3/2005 | Gerlach et al. | |
| 2005/0080421 A1 | 4/2005 | Weaver et al. | |
| 2005/0107796 A1 | 5/2005 | Gerlach et al. | |
| 2005/0124994 A1 | 6/2005 | Berger et al. | |
| 2005/0149027 A1 | 7/2005 | Campbell et al. | |
| 2005/0154392 A1 | 7/2005 | Medoff et al. | |
| 2005/0159753 A1 | 7/2005 | Kitchens | |
| 2005/0165400 A1 | 7/2005 | Fernandez | |
| 2005/0192576 A1 * | 9/2005 | Michelson | 606/61 |
| 2005/0246021 A1 | 11/2005 | Ringeisen et al. | |
| 2006/0058798 A1 * | 3/2006 | Roman et al. | 606/71 |
| 2006/0149263 A1 | 7/2006 | Newcomb et al. | |
| 2006/0195085 A1 * | 8/2006 | Happonen et al. | 606/61 |
| 2006/0200134 A1 | 9/2006 | Freid et al. | |
| 2006/0235399 A1 | 10/2006 | Carls et al. | |
| 2006/0235405 A1 * | 10/2006 | Hawkes | 606/69 |
| 2007/0027230 A1 | 2/2007 | Beyar et al. | |
| 2007/0055257 A1 | 3/2007 | Vaccaro et al. | |
| 2007/0088362 A1 | 4/2007 | Bonutti et al. | |
| 2007/0162016 A1 | 7/2007 | Matityahu | |
| 2007/0173843 A1 | 7/2007 | Matityahu | |
| 2008/0300637 A1 | 12/2008 | Austin et al. | |
| 2008/0306550 A1 | 12/2008 | Matityahu | |

FOREIGN PATENT DOCUMENTS

| | | | |
|---|---|---|---|
| JP | 2002-345836 | | 3/2002 |
| WO | 95/35067 | | 12/1995 |
| WO | 99/05968 | | 2/1999 |
| WO | 03/002022 | | 1/2003 |
| WO | 03055401 | | 7/2003 |
| WO | WO 2004/084701 | * | 2/2004 |
| WO | 2004/062482 | | 7/2004 |
| WO | WO 2004084701 A2 | * | 10/2004 |
| WO | 2005/053550 | | 6/2005 |
| WO | WO 2007/050796 | | 5/2007 |

OTHER PUBLICATIONS

Instructional Letter to Australian Associate in response to Oct. 19, 2011 Official Action issued by the Australian Patent Office for patent application serial No. 2006306120, Sep. 6, 2012, pp. 1-9.

Official Action issued by the Australian Patent Office issued by the Australian Patent Office for AU patent application serial No. 2006306120, Oct. 19, 2011, pp. 1-4.

Official Action issued by the Canadian Patent Office for CA patent Application Serial No. 2,633,659, Feb. 21, 2013, pp. 1-3.

Official Action issued by the Canadian Patent Office for CA patent Application Serial No. 2,626,145, Sep. 21, 2012, pp. 1-5.

Transmittal Letter from Chinese Associate dated Jan. 12, 2012 for Dec. 21, 2011 Official Action issued by the Chinese Patent Office for CN patent application serial No. 201110079239.9, Dec. 23, 2011, pp. 1-13.

Supplementary European Search Report issued by the European Patent Office for EP Application No. 08730998, Jul. 5, 2012, pp. 1-6.

Instructional Letter to the foreign associate in response to the Feb. 12, 2013 Examination Report issued by the European Patent Office for EP Application No. 06840346.8 (Aug. 16, 2013) pp. 1-5.

Examination Report issued by the European Patent Office for EP Application No. 06840346.8 (Feb. 12, 2013) pp. 1-4.

Reporting Email from European Associate for EP Patent Application No. 06840346.8, Dec. 23, 2011, pp. 1-2.

Examination Report issued by the European Patent Office for EP patent application serial No. EP 06840346.8, Nov. 30, 2011, 1-4.

Examination Report issued by the European Patent Office for EP Patent Application No. 06817405.1, Jun. 17, 2013, pp. 1-4.

Response to Nov. 6, 2012 Examination Report issued by the European Patent Office for EP patent application serial No. 06817405.1 (May 15, 2013) pp. 1-2.

(56) References Cited

OTHER PUBLICATIONS

Examination Report issued by the European Patent Office for EP Patent Application No. 06817405.1, Nov. 6, 2012 pp. 1-4.
Filed Response to Mar. 1, 2012 Examination Report issued by the European Patent Office for EP patent application serial No. 06817405.1, Apr. 18, 2012, pp. 1-5.
Examination Report issued by the European Patent Office for EP Patent Application No. 06817405.1, Mar. 1, 2012, pp. 1-4.
Instructional Letter to European Associate in response to Jul. 11, 2011 Supplementary European Search Report for EP Patent Office application serial No. EP 06817405.1, Jan. 28, 2012, pp. 1-3.
Instructional Letter for Response to Dec. 26, 2011 Official Action for Japanese Patent Application No. 2008-537954, Jun. 25, 2012 pp. 1-6.
Official Action issued by the Japanese Patent Office for JP patent application serial No. 2008-537954, Dec. 26, 2011 pp. 1-3.
Transmittal Letter from Chinese Associate dated Jan. 12, 2012 for Dec. 21, 2011 Official Action issued by the Chinese Patent Office for CN patent application serial No. 201100792399, Dec. 23, 2011, pp. 1-13.
Apr. 6, 2009 Non-Final Rejection issued by the U.S. Patent Office for corresponding U.S. Appl. No. 11/588,037; pp. 1-16.
Jul. 2, 2009 Amendment to Apr. 6, 2009 Non-Final Rejection for corresponding U.S. Appl. No. 11/588,037; pp. 1-15.
Nov. 13, 2009 Non-Final Rejection issued by the U.S. Patent Office for corresponding U.S. Appl. No. 11/588,037; pp. 1-16.
Mar. 2, 2010 Amendment to Nov. 13, 2009 Non-Final Rejection for corresponding U.S. Appl. No. 11/588,037; pp. 1-13.
Jun. 24, 2010 Non-Final Rejection issued by the U.S. Patent Office for corresponding U.S. Appl. No. 11/588,037; pp. 1-17.
Oct. 25, 2010 Amendment to Jun. 24, 2010 Non-Final Rejection for corresponding U.S. Appl. No. 11/588,037; pp. 1-18.
Jan. 3, 2011 Final Rejection issued by the U.S. Patent Office for corresponding U.S. Appl. No. 11/588,037; pp. 1-15.
Feb. 23, 2011 Amendment to Jan. 3, 2011 Final Rejection issued by U.S. Patent Office for U.S. Appl. No. 11/588,037; pp. 1-5.
Mar. 4, 2011 Notice of Allowance issued by the U.S. Patent Office for corresponding U.S. Appl. No. 11/588,037; pp. 1-6.
Apr. 6, 2009 Non-Final Rejection issued by the U.S. Patent Office for corresponding U.S. Appl. No. 11/644,433; pp. 1-13.
Oct. 6, 2009 Amendment to Apr. 6, 2009 Non-Final Rejection for corresponding U.S. Appl. No. 11/644,433; pp. 1-9.
Jan. 4, 2010 Final Rejection issued by the U.S. Patent Office for corresponding U.S. Appl. No. 11/644,433; pp. 1-16.
Mar. 1, 2010 Amendment After Final to Jan. 4, 2010 Final Rejection for corresponding U.S. Appl. No. 11/644,433; pp. 1-10.
Sep. 2, 2011 Notice of Allowance issued by the U.S. Patent Office for corresponding U.S. Appl. No. 11/644,433; pp. 1-8.
Translation of Sep. 4, 2009 Official Action issued by the Chinese Patent Office for corresponding CN patent application No. 200680039692.4, pp. 1-17.
Mar. 3, 2010 Instructional letter in response to Sep. 4, 2009 Official Action for corresponding CN patent application No. 200680039692.4, pp. 1-11.
Translation of Sep. 20, 2010 Official Action issued by the Chinese Patent Office for corresponding CN patent application No. 200680039692.4, pp. 1-10.
Oct. 19, 2010 Instructional letter in response to Sep. 20, 2010 Official Action for corresponding CN patent application No. 200680039692.4, pp. 1-5.
Translation of Jan. 22, 2010 Official Action issued by Chinese Patent Office for corresponding CN patent application No. 20068005257.8, pp. 1-9.
Apr. 29, 2008 International Preliminary Report on Patentability issued by the International Bureau of WIPO for corresponding PCT patent application serial No. PCT/US2006/041850, pp. 1-5.
Jun. 24, 2008 International Preliminary Report on Patentability issued by the International Bureau of WIPO for corresponding PCT application serial No. PCT/US2006/062577, pp. 1-5.
Dec. 7, 2009 International Preliminary Report on Patentability issued by the International Bureau of WIPO Office for corresponding patent application serial No. PCT/US2008/055338, pp. 1-7.
Mar. 28, 2011 Supplementary European Search Report issued by the European Patent Office for patent application serial No. EP 06840346.8, pp. 1-5.
Jun. 29, 2011 Supplementary European Search Report issued by the European Patent Office for corresponding patent application serial No. EP 06817405.1, pp. 1-8.
Examiner Initiated Interview Summary mailed Jul. 8, 2009 for U.S. Appl. No. 11/588,037, filed Oct. 25, 2006, pp. 1-2.
Examiner Initiated Interview Summary mailed Mar. 15, 2010 for U.S. Appl. No. 11/588,037, filed Oct. 25, 2006, pp. 1-4.
International Search Report and Written Opinion for Application No. PCT/US2006/041850, mailed on Sep. 13, 2007, pp. 1-5.
International Search Report and Written Opinion for Application No. PCT/US2008/055338, mailed on Oct. 9, 2008, pp. 1-8.
Notice of Allowance and Applicant Initiated Interview Summary mailed Aug. 26, 2013 for U.S. Appl. No. 13/037,206, filed Feb. 28, 2011, pp. 1-11.
Notice of Allowance mailed Jul. 18, 2013 for U.S. Appl. No. 13/037,206, filed Feb. 28, 2011, pp. 1-13.
Office Action mailed Dec. 23, 2011 with Transmittal Letter and Comments from Chinese Associate for Chinese Patent Application No. 201110079239.9, pp. 1-13 (English Translation).
Requirement for Restriction/Election mailed Apr. 11, 2013 for U.S. Appl. No. 13/037,206, filed Feb. 28, 2011, pp. 1-7.
Response mailed Feb. 7, 2012 for Extended European Search Report dated Jul. 11, 2011/Jul. 28, 2011 for European Patent Application No. 06817405.1 filed Oct. 25, 2006, pp. 1-10.
Response mailed Jun. 8, 2012 for Examination Report dated Nov. 30, 2011 for European Application No. 06840346.8 filed Dec. 22, 2006, pp. 1-4.
Response mailed Jun. 11, 2013 for Requirement for Restriction/Election dated Apr. 11, 2013 for U.S. Appl. No. 13/037,206, filed Feb. 28, 2011, pp. 1-5.

* cited by examiner

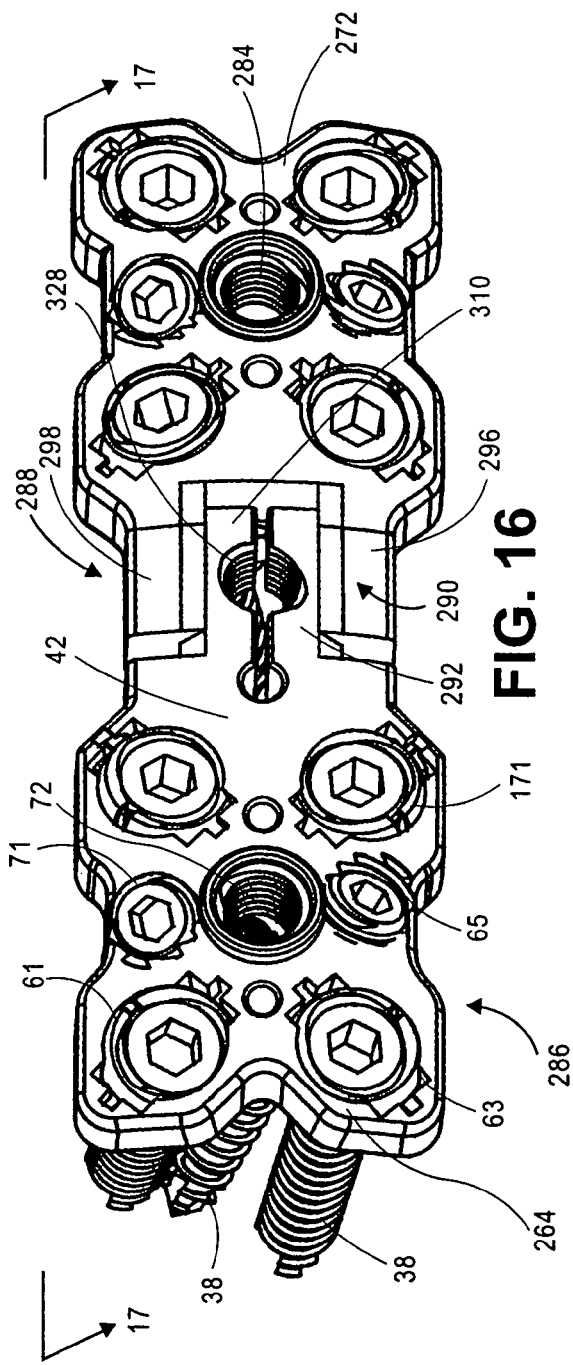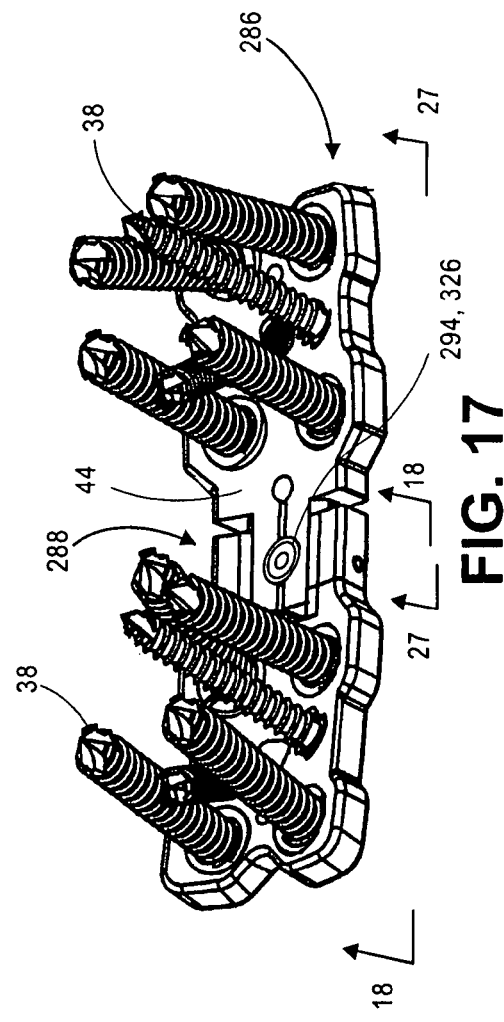

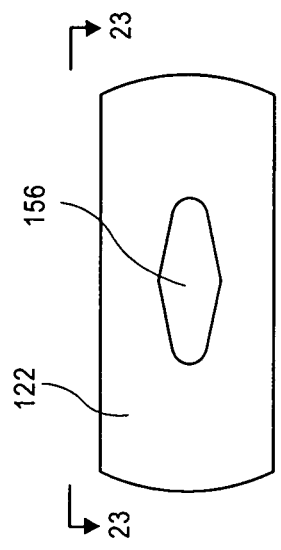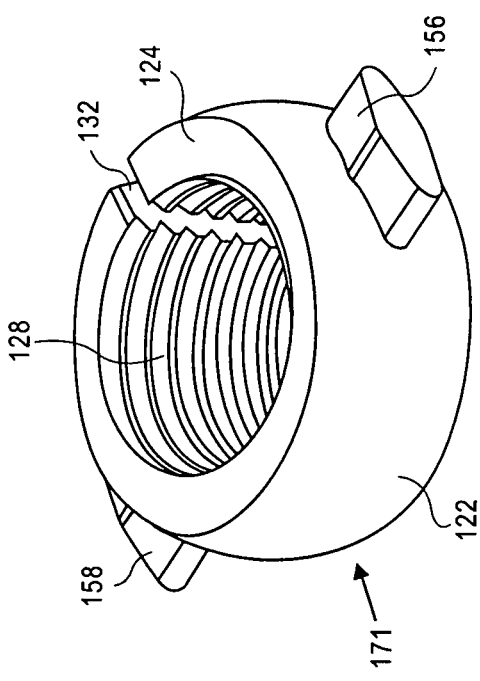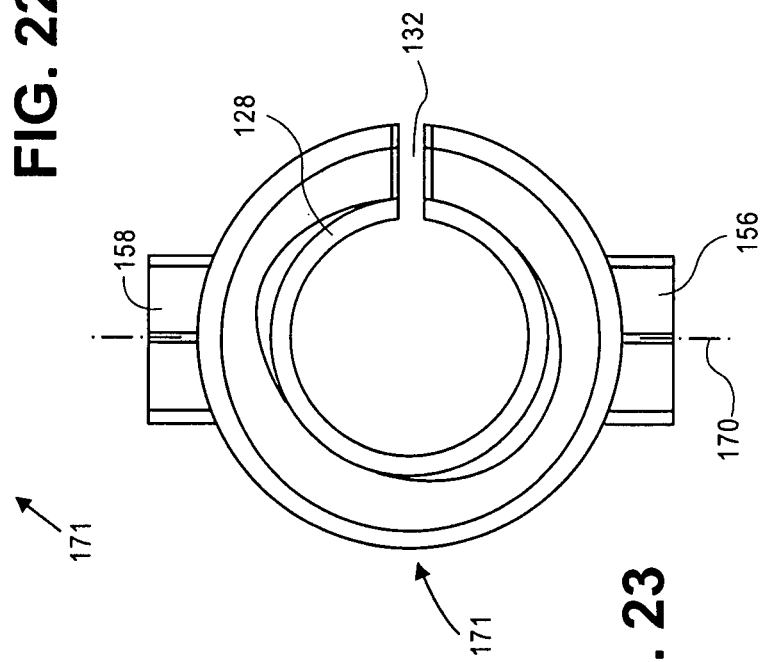

SPINE REPAIR ASSEMBLY

SCOPE OF THE INVENTION

The present invention relates to a spine repair assembly, and more specifically to an assembly and system for repair of cervical and thoraco-lumbar regions of the spine.

BACKGROUND

It is known to repair spinal injuries and correct spinal problems, specifically cervical related injuries, using a plate. Plates are typically affixed to one or more vertebral bodies using bone screws which thread through openings in the plate and into the vertebral bodies. Some bone screw and plate assemblies, unfortunately, require that the screw be inserted at a fixed insertion angle that is perpendicular to the plate. These plates are difficult to use due to the lack of variability in insertion angle. In poor quality bone these plates are prone to subsidence, decreased rate of fusion, and subsequent failure.

Other current systems do not provide a rigid attachment in the vertebral body. The screw head is able to toggle within the plate. The screws are therefore able to move within the vertebral body causing shear stress to the trabecular bone, which is weakest in shear. Bone screws are typically attached at a single point or two points of fixation. Thus, so long as the patient load is less than the shear frictional force, the construct of bone screw and plate is stable. However, because the screws have only one or two points of fixation, if the patient load at that location exceeds the shear frictional force, then the construct may be unstable and could potentially fail. Typically, in poor quality bone, minimal force is needed to pull out a plate with single points of fixation.

Accordingly, what is needed in the art is a spine repair system and assembly that is easy to attach and capable of locking the bone screw and plate, provides for a variable angle of attachment only in certain angles and has increased rigidity within the vertebral body.

SUMMARY OF THE INVENTION

A spine repair system and assembly are provided. The spine repair system includes a plate for use with a plurality of bone screws to treat a mammalian body having a plurality of vertebral portions in a spine. The plate has an elongate plate-like member having first and second end portions adapted for fastening respectively to a plurality of vertebral portions. First and second end portions are provided with a plurality of apertures for receipt of bone screws, including one or more apertures inclined relative to the plate-like member so as to enhance securement of the first and second end portions to the first and second vertebral portions when the bone screws are introduced through the screw holes into the vertebral portions.

BRIEF DESCRIPTION OF THE DRAWINGS

FIG. 16 is a top perspective view of a further embodiment of a spine plate of the present invention without its locking element but shown with a plurality of bone screws disposed therein.

FIG. 17 is a bottom perspective view of the spine plate of FIG. 16 taken along the line 17-17 of FIG. 16.

FIG. 21 is a perspective view of a bushing of the spine plate of FIG. 16.

FIG. 22 is an end view of the bushing of FIG. 21 taken along the line 22-22 of FIG. 21.

FIG. 23 is a top plan view of the bushing of FIG. 21 taken along the line 23-23 of FIG. 22.

DESCRIPTION OF THE INVENTION

Figure 1:
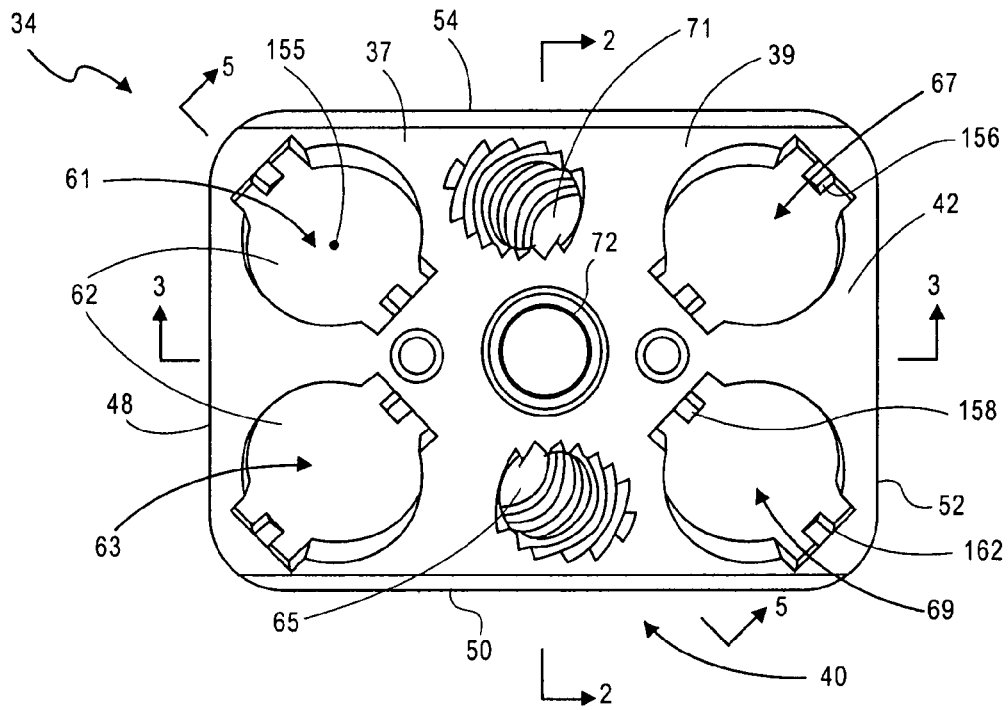
FIG. 1 is a top plan view of a spine plate of the present invention with the bushings and screws removed.

In general, the present invention relates to a spine repair assembly 32 that includes a spine plate 34, a plurality of adjustable attachment components or bushings 36 and a plurality of bone or attachment screws 38 for use with the spine plate 34. The angle of a bushing 36 relative to the spine plate 34 may be manipulated during certain surgeries so that an accompanying screw 38 extends into the bone being treated in the desirable orientation. This orientation can be constrained in one plane. For example, the axis about which the bone screw 38 pivots can be constrained to a single plane, such as the plane of the spine plate, and variable in another plane, for example the bone screw 38 can pivot about such pivot axis in a plane extending perpendicular to the plane of the spine plate. The spine repair assembly 32 can be used with any suitable bone of a mammalian body. The spine repair bone assembly 34 is described and illustrated herein for use with the bones or vertebrates of the spine of a mammalian body such as a human body.

Figure 2:
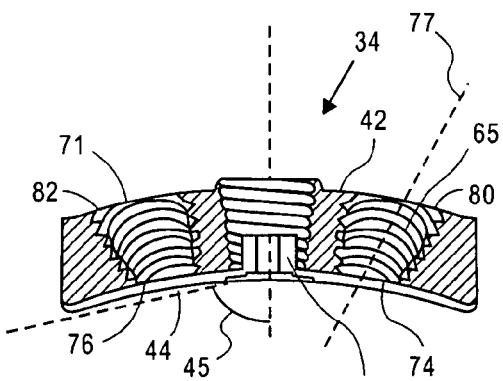
FIG. 2 is a cross-sectional view of the spine plate of FIG. 1 taken along the line 2-2 of FIG. 1.

Spine plate 34 is a static cervical spine plate formed from an elongate body 40 made from any suitable material, such as a resorbable, composite or metal material, and is preferably made from stainless steel or titanium. Spine plate 34, as can be seen from FIGS. 1-4, has an elongate plate-like member or body 40 with first and second end portions 37, 39 adapted for fastening respectively to first and second vertebral portions. Elongate body 40 has a first or outer surface 42 and a second or inner surface 44 spaced a distance from the first surface 42 by the thickness 46 of spine plate 34. Spanning between the first surface 42 and the second surface 44 are a first side surface 48, a second side surface 50, a third side surface 52 and a fourth side surface 54. The first surface 42 of spine plate 34 is preferably anatomically contoured to the vertebral bodies being treated. In one preferred embodiment, the first surface 42 is concave, as illustrated in FIG. 2, while the second surface 44 is convex. In a preferred embodiment, the degree 45 of concavity is preferably 12 degrees centered over centerline 78. However, variations in the contour of the first surface and second surface would not depart from the overall scope of the present invention. For example, a spine plate 34 having a contoured first surface 42 and a planar second surface 44 may be acceptable for the purposes provided. The one or more side surfaces 48, 50, 52, 54 can each be planar. Alternatively, any one or more of side surfaces 48, 50, 52, 54 may have a recess portion 60 or groove.

Spine plate 34 is provided with a plurality of apertures or holes extending between surfaces 42 and 44 for directly or indirectly receiving bone screws 38. More specifically, the first end portion 37 is provided with first, second and third screw holes or apertures 61, 63, 65. Second end portion 39 is provided with fourth, fifth and sixth screw holes or apertures 67, 69, 71. In this regard, some or all of such holes can be configured to receive a bushing 36 so as to indirectly receive a bone or attachment screw 38 and some or all of such holes may be configured with an inner thread. It is understood that any combination of threaded and bushing-receiving holes or apertures can be provided. In the illustrated static cervical spine plate 34 a plurality of apertures, more specifically first and second screw holes 61, 63 and fourth and fifth screw holes 67, 69, are provided in the spine plate 34 for receipt of a bushing 36, and a plurality of threaded apertures, more specifically third and sixth screw holes 65, 71, are provided in the spine plate 34. The apertures 61, 63, 67 and 69 and threaded apertures 65 and 71 extend through the spine plate 34 from the vertebrate facing surface 42 to the outer surface or face 44.

Threaded apertures 65 and 71 in the spine plate 34 can be arranged in any suitable configuration or array, and can vary in number and location. In one embodiment, threaded apertures 65 and 71 of the spine plate 34 are spaced apart transversely along a transverse centerline 66 which extends from the second side surface 50 to the fourth side surface 54 (see FIG. 4). Threaded apertures 65, 71 are also spaced longitudinally of the first and second screw holes 61, 63 and the fourth and fifth screw holes 67, 69, respectively. The plurality of threaded apertures 65, 71 in the embodiment shown in FIGS. 1-4 includes an array of threaded apertures having a first inclined aperture 71, a second included aperture 65 and a threaded tool engaging aperture 72. As best seen in FIG. 2, the first inclined aperture 71 and the second inclined aperture 65 taper inwardly from the outer face 42 to inner face 44 and have an inner thread 88 of constant depth extending the length of the aperture. The tapered diameter of apertures 71 and 65 tapers to accommodate the head 224 of bone screw 38. The tapered diameter of apertures 71 and 65 is preferably twelve degrees centered over axial centerline 77. Inner thread 88 is adapted to receive a threaded screw 38. In one preferred embodiment the apertures 71 and 65 are threaded in a direction that permits the rotational threaded insertion of a bone screw 38 from the outer surface 42 through the plate 34 to the inner vertebrate facing surface 44. More specifically, as first and second inclined apertures 71 and 65 have an inwardly tapered shape, the inner thread 88, and first end 74, 76 has a first diameter 90 which is wider than the second diameter 92 at the second end 80, 82 of the aperture. Accordingly, as the aperture tapers inwardly, the inner thread 88 likewise tapers inwardly.

Figure 5:
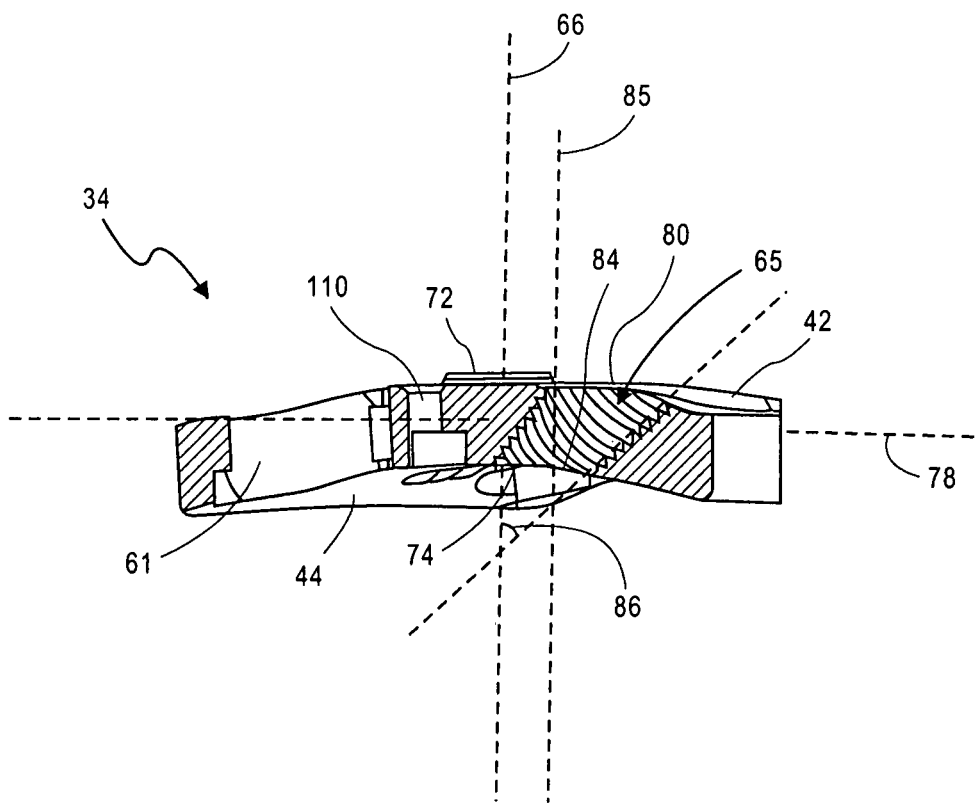
FIG. 5 is cross-sectional view of the spine plate of FIG. 1, taken along the line 5-5 of FIG. 1.
Figure 7:
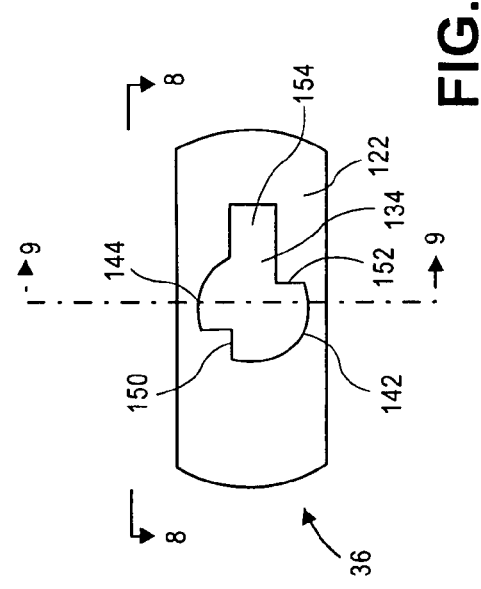
FIG. 7 is an end view of the bushing of FIG. 6 taken along the line 7-7 of FIG. 6.
Figure 6:
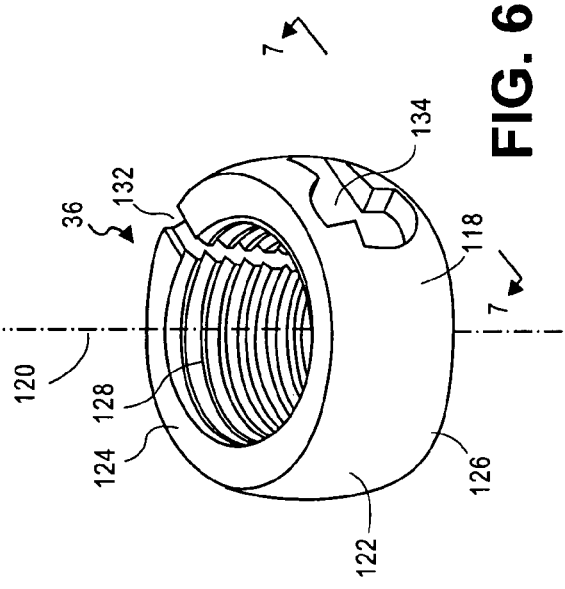
FIG. 6 is a perspective view of a bushing of the spine plate of FIG. 1.
Figure 9:
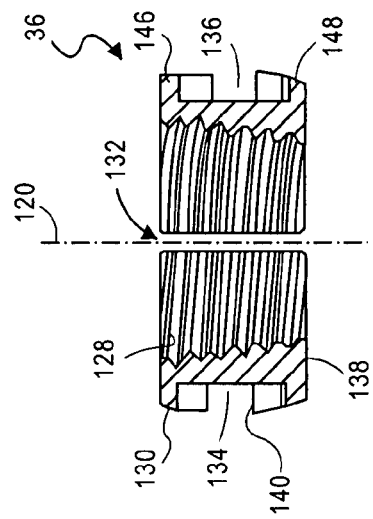
FIG. 9 is a cross-sectional view of the bushing of FIG. 6 taken along the line 9-9 of FIG. 7.
Figure 8:
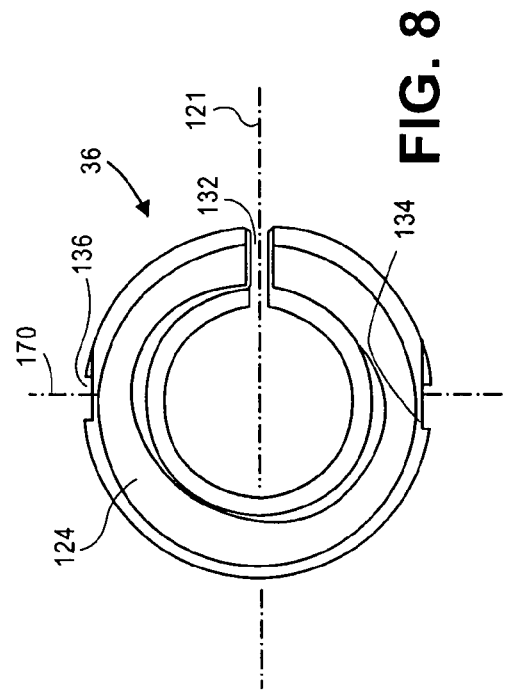
FIG. 8 is a top plan view of the bushing of FIG. 6 taken along the line 8-8 of FIG. 7.

First and second angled or inclined apertures 71 and 65 are inclined relative to the plate-like member or body 40. The angle of inclination 84, 86 of threaded bores 65 and 71 is fixed in relation to plate-like member 34 (see FIG. 5). For ease of reference, the inclined aperture is discussed and shown specifically with reference to inclined aperture 65, but may be equally applied to inclined aperture 71 with the exceptions noted hereinbelow. The first angled or inclined aperture 71 and the second angled or inclined aperture 65 are inclined at a first angle 84 relative to an imaginary line 85 extending normal to surfaces 42 and 44, as shown in FIG. 5. The first angle of inclination 84, shown in FIG. 5, ranges from 0 to 45 degrees, preferably from 15 to 30 degrees and is more preferably approximately 30 degrees from imaginary line 85. A second angle of inclination 86 is also provided for each of first and second threaded bores 65 and 71, and is inclined so that the first ends 74, 76 of the first inclined aperture and the second inclined apertures 71, 65 are closer in proximity to a longitudinal centerline 78 than the second ends 80, 82 of the first angled aperture and second angled apertures. Second angle of inclination 86 for each of bores 65 and 71 extends at an angle ranging from 0 to 60 and more preferably from 42 degrees to 45 degrees relative to transverse centerline 66. In this manner, the second angle of inclination for bore 65 is approximately opposite the second angle of inclination of bore 71. Thus, each of the threaded bores 65 and 71 is ramped inwardly away from transverse centerline 66 and toward longitudinal centerline 78. While specific first and second angles of inclination are described herein, it is understood that variations therefrom would be acceptable for the purposes provided.

Figure 3:
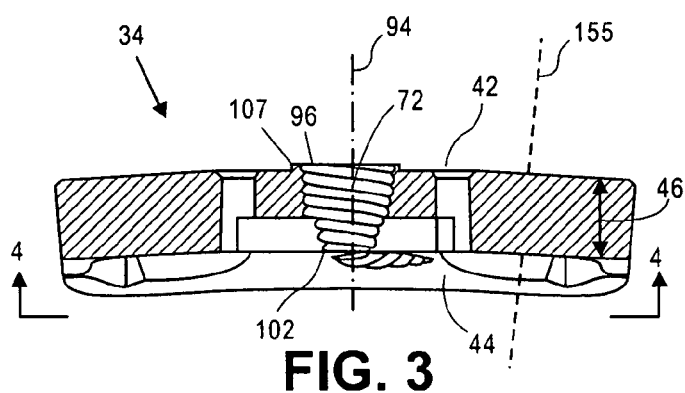
FIG. 3 is a cross-sectional view of the spine plate of FIG. 1 taken along the line 3-3 of FIG. 1.
Figure 4:
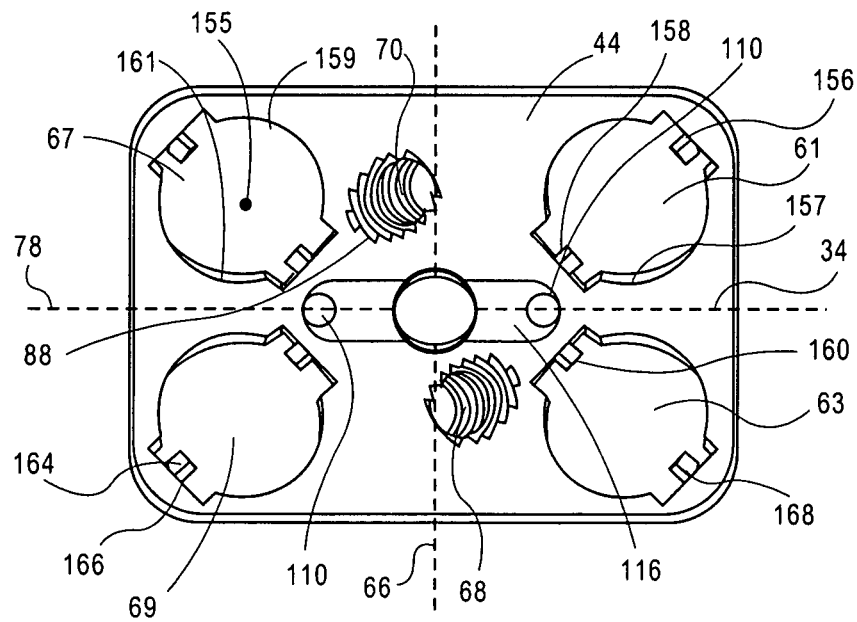
FIG. 4 is a bottom plan view of the spine plate of FIG. 1 taken along the line 4-4 of FIG. 3.

Threaded tool engaging aperture 72, as illustrated in FIG. 3, is positioned along an axis 94 extending perpendicular to first surface 42 and second surface 44. In one preferred embodiment, the tool engaging aperture 72 is positioned between the first inclined aperture 71 and the second inclined aperture 65. More specifically, the tool engaging aperture 72 is positioned at or near the center of spine plate 34. Threaded tool engaging aperture 72 is inwardly tapered so that its first end 96 has a diameter which is greater than the diameter of the second end 102. In a preferred embodiment the outer diameter may range from four to eight millimeters The degree 103 of taper of the tool engaging aperture centered upon axis 105 of the aperture 72 is preferably twelve degrees, although variations therefrom would be acceptable for the purposes provided. The tool engaging aperture 72 has an inner thread 104 that extends from the first end 96 to the second end 102 and is threaded for the insertion of or adapted to receive a tool or on its outer surface 42. A shoulder 107 is provided circumferentially surrounding aperture 72 at first end 96 of the aperture 72, extending above the outer surface 42. Preferably, shoulder 107 extends a minor amount, and more preferably between zero and one millimeters above outer surface 42. One or more smaller apertures or anchoring holes 110 may be provided extending through the spine plate 34 on first and second sides 112 and 114 for receipt of an anchoring device. A recess 116 may also extend along a length of the elongate body 40 centered between the first inclined aperture and the second inclined aperture 65 on vertebrate facing surface 44 for purposes of drug delivery. Holes 110 may also be used to introduce a medicament, such as but not limited to, a drug, into recess 116 after the device 34 has been secured into position on the spine.

Each of bushings 36 is made from a cylindrical or tubular body 118, illustrated in FIGS. 6-9, that is formed from any suitable material such as a composite material or a metal and is preferably made from stainless steel or titanium. The tubular bodies 118 of bushings 36 are sized for placement in apertures 61, 63, 67, 69. The bushings 36 are substantially as described in Applicant's co-pending U.S. patent application Ser. No. 11/588,037, filed Oct. 25, 2006, which is hereby incorporated by reference in its entirety. Generally, the tubular body 118 has an axial centerline 120 and a transverse centerline 121. The tubular body 118 has an outer annular wall 122 with top and bottom planar surfaces 124 and 126 so as to be substantially planar in conformation. An internally-threaded bore 128 is formed by wall 122 and extends along vertical centerline 120. The threads of bore 128 preferably taper inwardly toward the axial centerline 120 as they extend from top surface 186 to bottom surface 126 of the bushing 36. The body 118 is substantially cylindrical along the centerline 120. Outer surface 130 of annular wall 122 extends around the centerline 120 and is longitudinally convex relative to the centerline so as to have an outwardly-bowed arcuate shape. An opening, gap or slit 132 extends between threaded bore 128 and outer surface 130 along the transverse centerline 121 and in a direction parallel to the axial centerline 120.

Bushing 36 is provided with first and second transversely-aligned recesses 134 and 136 that are diametrically-aligned relative to annular wall 122 and extend substantially perpendicular to transverse centerline 121 of the bushing 36. In one embodiment, each of recesses 134 and 136 is formed by a planar base 138 extending perpendicular to a radian of the tubular body 118. The base 138 of recess 134 is preferably parallel of the base 138 of recess 136. Each of the recesses 134 and 136 can be shaped to include a bottom surface 140, which is part of a lower ramped surface 142, and an upper ramped surface 144. Annular wall 122 is formed with upper and lower shoulders 146 and 148. The shoulders 146 and 148 have respective upper and lower limiting surfaces 150 and 152. A slot 154 is provided for each recess in the annular wall 122 and commences where base 138 intersects outer surface 130 for serving as an entrance to the recess.

Bushing-receiving apertures 61, 63, 67 and 69 are provided in spine plate 34 in any suitable array (see FIGS. 1-4). As with the bushings 36, bushing receiving apertures 61, 63, 67, and 69 are substantially as described in Applicant's co-pending U.S. patent application Ser. No. 11/588,037, which is herein incorporated in its entirety by reference. Generally, the plurality of apertures are spaced apart in an array, and arranged for positioning of a bone screw 38 into corresponding vertebral bodies. Aperture 61 is centered on the vertical centerline 155 of the aperture 61 and is arcuate and preferably concave relative to the centerline 155. More preferably, the arcuate shape of inner surface 157 approximates the arcuate shape of bushing outer surface 130. Body 40 is provided with a circumferentially-extending ridge 159, 161 around each of the upper and lower ends of the aperture 61 adjacent respective outer and inner faces 42 and 44 of the body 40. Each of the apertures 61, 63, 67 and 69 is provided with first and second transversely-aligned pins 156 and 158 which extend inwardly into the aperture in opposite-facing diametric alignment. First and second pins 156 and 158 can be of any suitable type, which can also be referred to as outcrops, protuberances, projections, bulges, knobs, shelves or taps, are each preferably in the form of a wing. Each of such wings 156 and 158 can be of any suitable shape and in one embodiment, when viewed from its end, tapers inwardly in a forward direction from its center 160 to a forward winged portion 162 and tapers in a rearward direction from its center 160 to a rearward winged portion 164. Each of the winged portions 162 and 164 is formed from first and second ramped surfaces 166 inclined at an angle relative to longitudinal centerline of the winged portion. Further, other suitable pin and socket mechanisms can be provided with one or more pins provided on one of the spine plate and the bushing and one or more sockets provided on the other of the spine plate and the bushing. Such mechanisms can serve to restrict the pivot axis 170 of the bushing to a plane extending in the plane of the spine plate, or be more limiting so as to restrict the pivot axis 170 to a line extending to the plane of the spine plate. The spine plate assembly 32 can be configured to include cooperating engaging means which can be in the form of the mechanisms discussed above or any other suitable configuration for limiting the axis about which the bone screws pivot, whether such axis is in the plane of the spine plate or otherwise.

The placement of a bushing 36 and aperture 61 will now be described and is substantially as described in Applicant's co-pending U.S. patent application Ser. No. 11/588,037, which is incorporated herein in its entirety by reference. Generally, in one such placement method, each bushing 36 is aligned vertically relative to outer surface 42 of the body 40, that is the plane of the bushing extends perpendicular to the plane of the spine plate, and slots 154 on opposite sides of the bushings are aligned with the forward winged portion 162 of respective first and second wings 156 and 158 provided in the spine plate. The bushing 36 is moved forwardly into the spine plate, guided by wings 156 and 158 traveling through slots 154 into respective first and second recesses 134 and 136, until the forward winged portion 162 of the wings 156 and 168 engages bottom surface 140 of the recesses 134 and 136. Thereafter, bushing 36 is rotated, guided by the travel of the forward winged portion 162 of first and second wings 156 and 168 on lower ramped surface 142 of the recesses, until the bushing is disposed in a horizontal position such that the plane of the bushing is in the plane of the spine plate. Concurrently, the concave internal surface 157 of body 40 engages the convex outer surface 130 of the bushing 36. Spine plate internal surface 157 has a radial dimension that is slightly smaller then the radial dimension of bushing outer surface 130 so as to exert a compressive radial force against the bushing as the bushing is rotated from its vertical position to its horizontal position within aperture 61. Slit 132 in the bushing permits elongate body 118 of the bushing to radially contract during such rotation. The cooperatively similar contours of aperture internal surface 157 and bushing outer surface 130 facilitate a smooth compression and contraction of the bushing 36. The seated bushing is under slight radial compression from the engagement of the spine plate internal surface 157 with the bushing outer surface 130.

Once bushing 36 has been so placed within aperture 61, the bushing can rotate or pivot through a limited range of motion about pivot axis 170, which passes through the centers of first and second recesses 134 and 136. The capture of first and second wings 156 and 158 of the aperture 61 within the respective recesses 134 and 136 fixes pivot axis 170 with respect to spine plate 34. The engagement of top ramped surface 166 or bottom ramped surface 168 of the aperture 61 with respective upper limiting surface 150 or lower limiting surface 152 limits the range of pivotable motion of the bushing within the spine plate in one direction. Preferably the pivotable motion is limited such that the entire convex outer surface 130 of the bushing is recessed within aperture 61 and continuously and fully engaged by the concave internal surface 157 of the spine plate. The angle of inclination of ramped surfaces 142 and 144 of the bushing can be varied to determine the range of pivotable motion of the bushing within the spine plate. In this manner, a variety of apertures with differently configured first and second wings 156 and 158 can be provided for easily selecting the desired range of pivotable motion of the bushing and thus the bone screw 38 utilized therewith. It is appreciated that the spacing between upper and lower limiting surfaces 150 and 152 relative to horizontal centerline 78 in the body 40 can also be adjusted to change the range of pivotal motion of a bushing 36 within the spine plate.

A portion of elongate body 40 may be substantially planar and thus extends in a plane. In general, each of apertures 61, 63, 67 and 69 restricts the axis about which bushing 36 pivots to a line extending in the plane of the body 40. More specifically, each of the bushings can only pivot about an axis extending in the plane of the body 40.

Upper and lower ridges 159, 161 of body 40 restrict bushing 36 from inadvertently separating from the spine plate during placement and manipulation of the bushing within the spine plate and during attachment of the spine plate to a bone of a patient. In this regard, body 40 has a thickness in the vicinity of each aperture 61 and bushing 36 and a thickness between top and bottom surfaces 124 and 126 that is less than the thickness of the spine plate in the vicinity of the aperture 61. After insertion of the bushing 36 into the spine plate 34, upper ridge 159 can be optionally punched or otherwise narrowed (not shown) so as to restrict the bushing from being rotated to a vertical position and thus removed from the spine plate 34.

Figure 19:
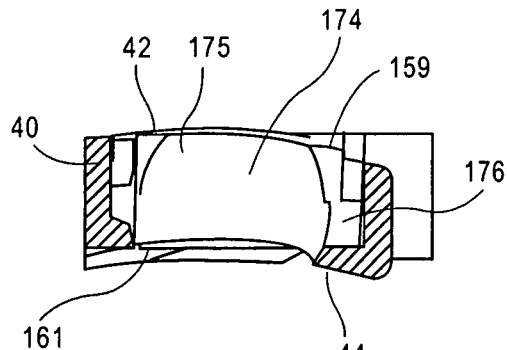
FIG. 19 is a cross-sectional view of the first portion of the spine plate of FIG. 18 taken along the line 19-19 of FIG. 18.
Figure 20:
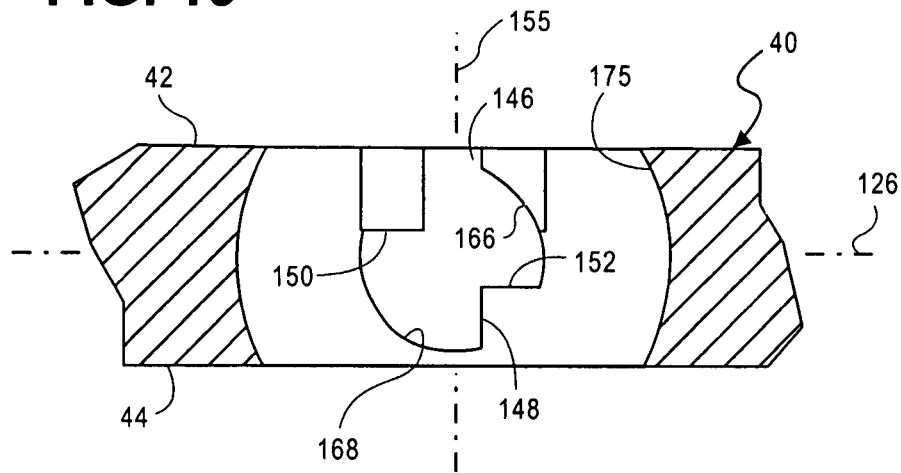
FIG. 20 is a cross-sectional view of the spine plate of FIG. 18 taken along line 20-20 of FIG. 18.
Figure 24:
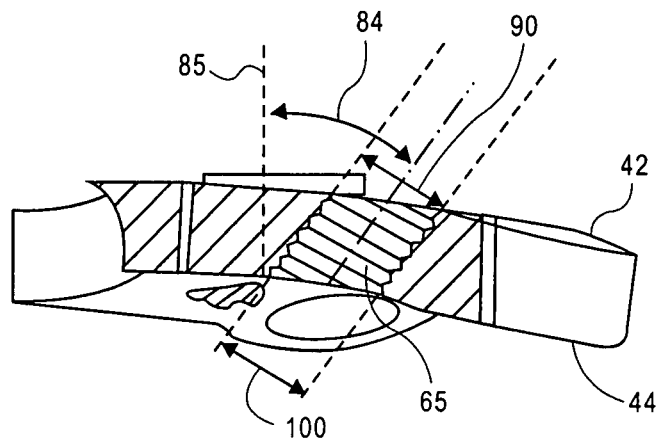
FIG. 24 is a cross-sectional view of the first portion of the spine plate of FIG. 18 taken along the line 24-24 of FIG. 18.
Figure 25:
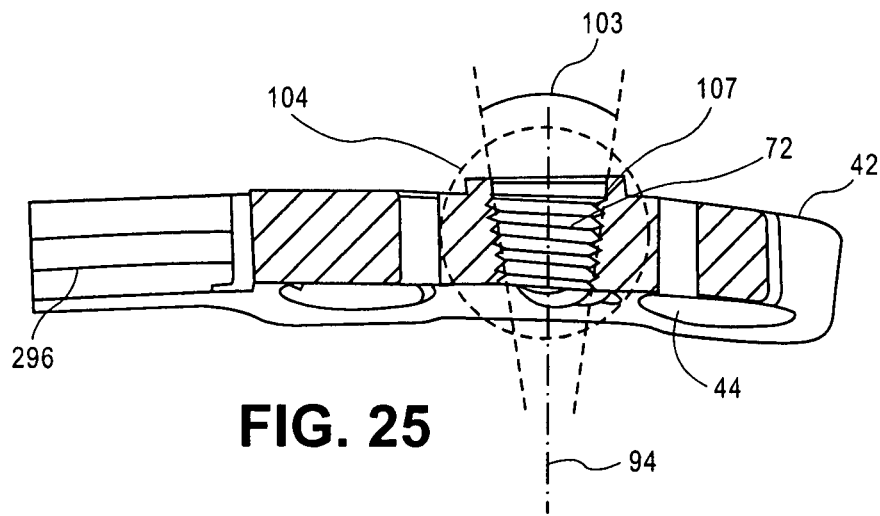
FIG. 25 is a cross-sectional view of the first portion of the spine plate of FIG. 18 taken along the line 25-25 of FIG. 18.
Figure 26:
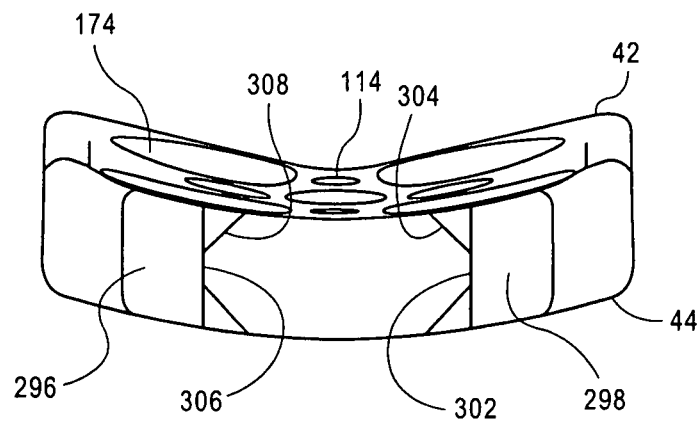
FIG. 26 is an end elevational view of the first portion of the spine plate of FIG. 18 taken along the line 26-26 of FIG. 18.
Figure 27:
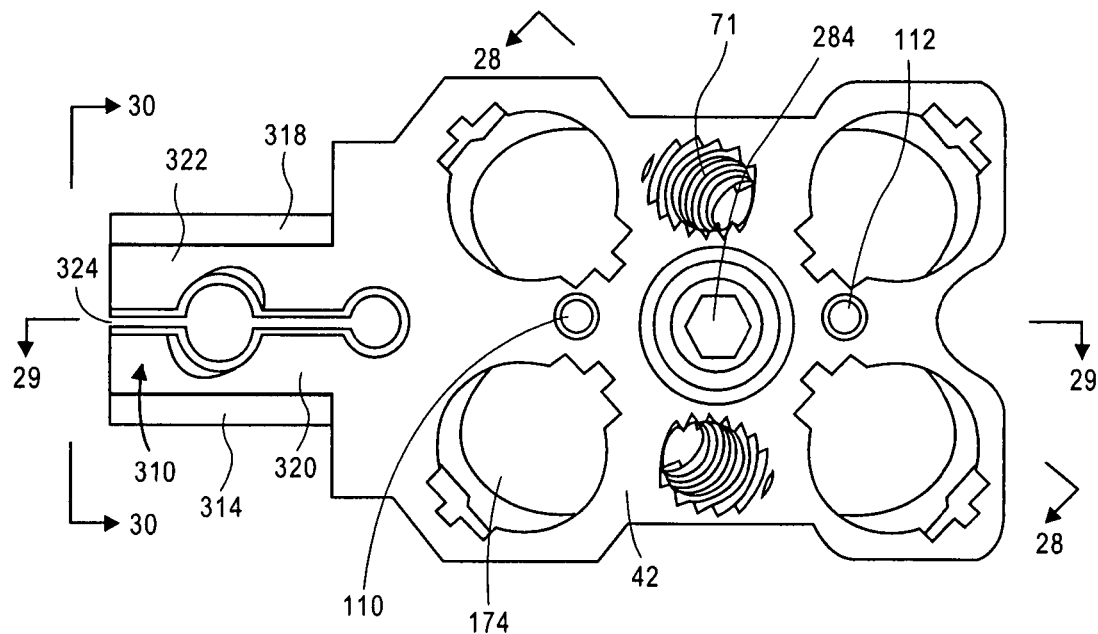
FIG. 27 is a top plan view, with the bushings and bone screws removed, of a second portion of the spine plate of FIG. 16 taken along the line 27-27 of FIG. 17.
Figure 28:
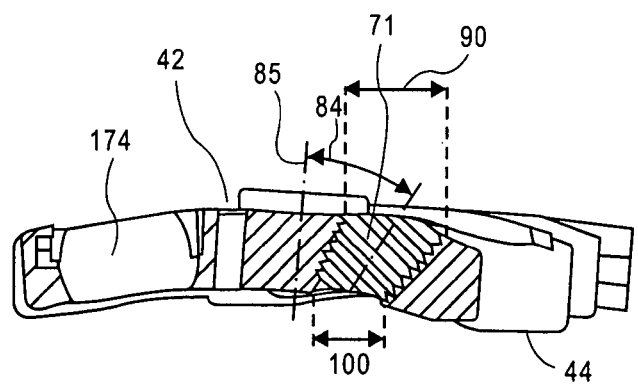
FIG. 28 is a cross-sectional view of the second portion of the spine plate of FIG. 27 taken along the line 28-28 of FIG. 27.

Other suitable embodiments of a bushing for use in a spine repair assembly of the present invention can be provided, including as described in Applicant's co-pending U.S. patent application Ser. No. 11/588,037, which is incorporated herein its entirety by reference. Generally, bushing 171, illustrated in FIGS. 19-21, is substantially similar to bushing 36 and like reference numerals have been used to describe like elements of bushing 171. Instead of having first and second transversely-aligned recesses, first and second transversely-aligned pins 156 and 158 extend horizontally outwardly from opposite sides of annular wall 122. Preferably, each of the pins 156 and 158 is vertically centered relative to top and bottom surfaces 124 and 126 so as to protrude from the outermost portion of the convex outer surface 130 and extend in a direction perpendicular to vertical centerline 120 or 155. The first and second wings 156 and 158 each include a center 160 and front and rear winged portions 162 and 164.

Figure 10:
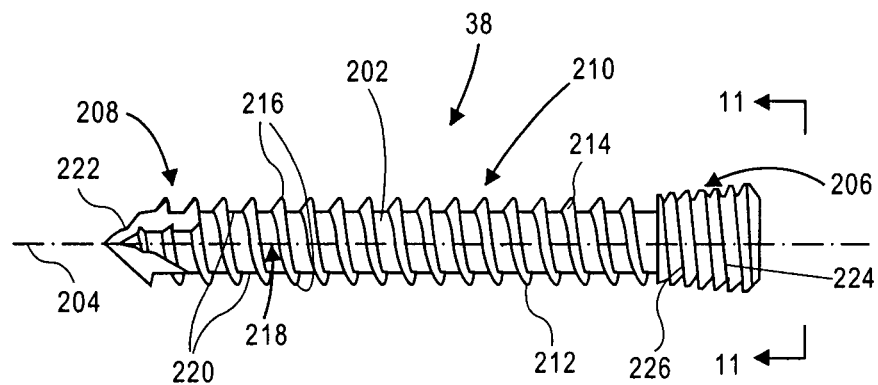
FIG. 10 is a side elevational view of a bone screw for use with the spine plate of FIG. 1.
Figure 11:
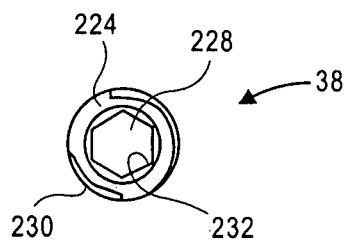
FIG. 11 is a proximal end view of the bone screw of FIG. 10 taken along the line 11-11 of FIG. 10.

Any suitable type of bone screw 38, solid or cannulated, may be used with spine repair assembly 32. One suitable type of bone screw 38 is illustrated in FIGS. 10-11 and is made from any suitable material such as a composite material or metal and is preferably made from stainless steel or titanium. The screw 38 includes an elongate shaft 202 extending along a longitudinal axis 204 and provided with external threads 212 having a helical ridge 214. Shaft 202 is further provided with a pointed distal tip 222 that is self tapping and optionally self drilling. A head 224 is joined to the proximal portion 206 of the shaft 202 by a neck 226. The head 224 is preferably tapered as it extends distally so as to be conically shaped and is preferably externally threaded. Head 224 may have a length ranging from two to five millimeters. Screw 38 can have a length ranging from 10 to 150 millimeters. Screws for use with the spine plate may vary in diameter. In one preferred embodiment, bone screws 38 having a first diameter are used and inserted into bushings 36 and screws having a second, smaller diameter are used and inserted into inclined threaded apertures 61, 65. However, variations on bone screw 38 dimensions would not depart from the purposes provided. For instance, bone screws 38 of equivalent diameter may be used for all threaded openings of the spine plate.

Head 224 is preferably formed with at least one drive socket 228 and centered on longitudinal axis. Drive socket 228 can be of any suitable type and is shown in FIGS. 10-11 as having an hexagonal or hex-head 230 configuration formed from six operable surfaces 232 extending parallel to axis 204. Other suitable configurations for drive socket 228 include a square-shaped configuration (not shown) and a star-shaped configuration (not shown), among others.

Figure 12:
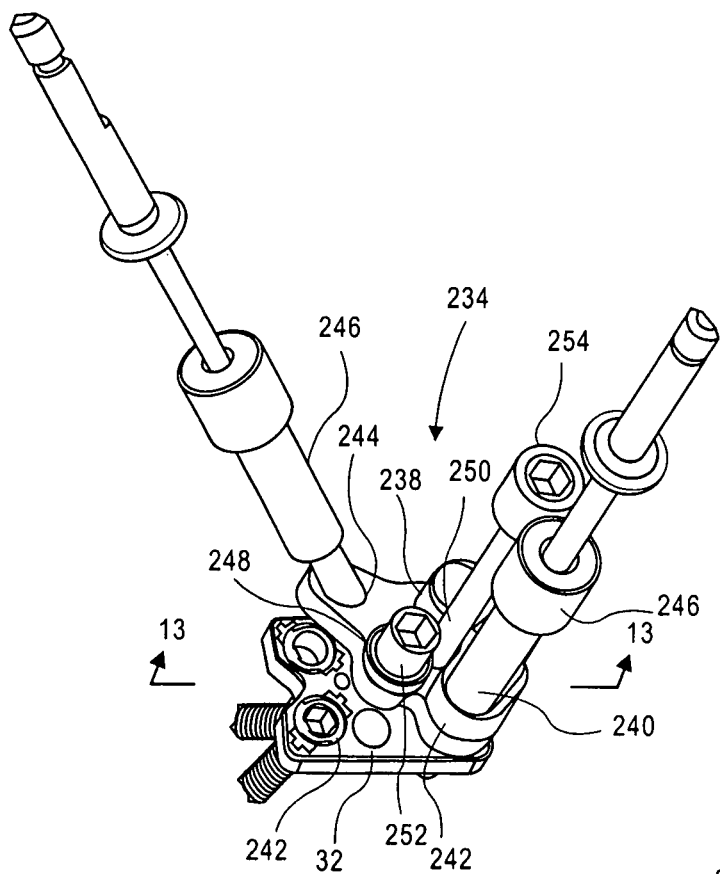
FIG. 12 is a perspective view of the spine plate of FIG. 1, with the bushings installed and several bone screws disposed therein, coupled to a jig assembly for installing the spine plate.
Figure 13:
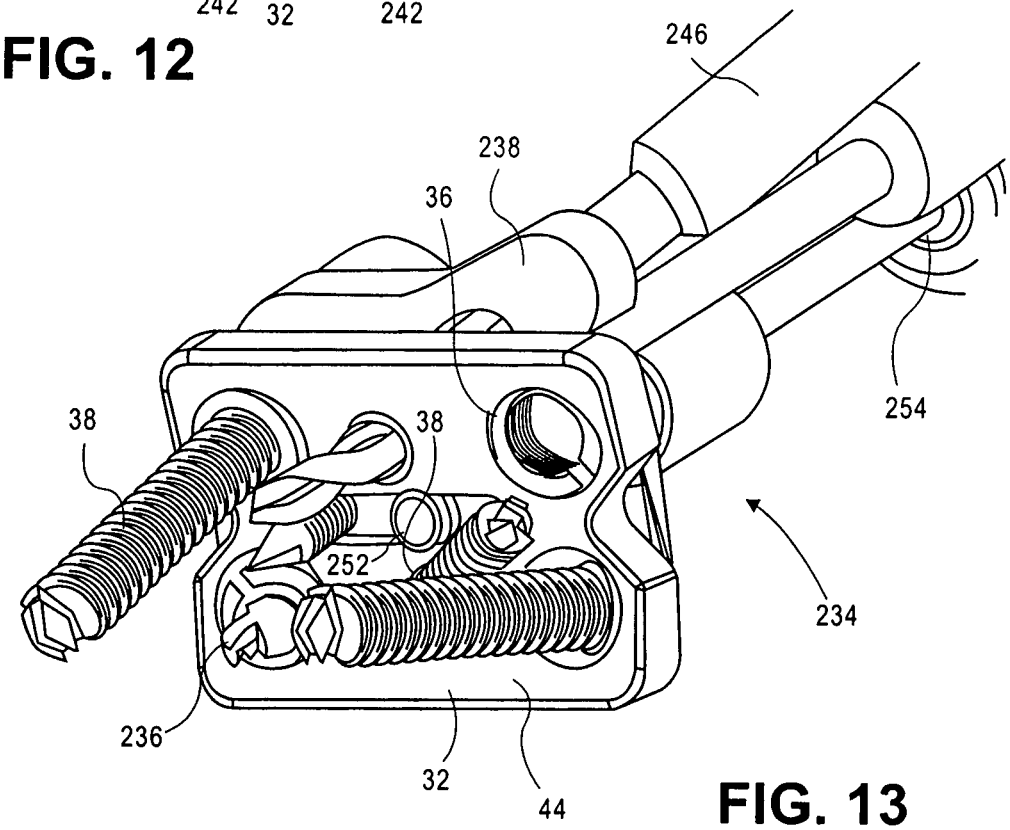
FIG. 13 is a bottom plan view of the spine plate and jig assembly of FIG. 12 taken along the line 13-13 of FIG. 12.

Jig 234, as shown in FIGS. 12-13, is used to place and attach the static cervical spine plate 34 to the vertebral bodies. Jig 234 is used to allow for targeting of the drill bits 236 within the holes of the plate. Jig 234 is formed from an attachment plate 238 with plurality of apertures therethrough. Jig 234, in one preferred embodiment, includes three primary holes or apertures 240, 242, 244 used for drilling and before placement of screws 38 into the vertebral body through the plate 34. More specifically, jig 234 has a pair of openings 240 and 242 which are trapezoidal and oblong to allow for receipt and movement of a drilling sleeve 246 along the axis of the plate 238 to guide a drill 236. The third targeting opening 244 of the jig 234 is provided for receipt of a third screw that is inserted into the vertebral body. This third opening accommodates a drilling sleeve 246 for the third screw 38 which is angled or inclined into the plate 34.

An additional two apertures 248, 250 are provided on the jig 234. The first aperture 248 is adapted to receive a pivot bolt 252 which both secures or tightens the jig 234 to the plate 34 and allows the jig 234 to rotate or pivot 180 degrees. Pivot bolt 252 threads through the attachment plate 238 and into spine plate 34 at threaded aperture 250 positioned in the spine plate. The aperture 250 is a centralized bore for receipt of a threaded member, such as pivot bolt 252, and is positioned so as to be centered in the plate 34 and thereby aligns the pilot holes 240, 242, 244 of the jig 234 with the apertures 61, 65 of the plate 34. This permits drilling and screw insertion into both ends of the plate. The threaded engagement secures the jig 234 to the spine plate 34 permitting the drilling of pilot holes and subsequent insertion of screws 38. Accordingly, a jig 234 having a pivot bolt 252 is capable of rotation relative to the plate 34 to attach the screws 38 to the first vertebral body and then attach the screws to a second vertebral body. A location pin 254 may also be provided in an additional aperture of the jig 234 to pre-fix the location of the jig 234. More specifically, a centralizing pin 254 fixes the jig 234 to the plate by providing a second position of contact with the plate 34. When secured with each of the foregoing pins, namely the pivot bolt 252 and the centralizing pin 254, the holes in the jig 234 are aligned with respect to the apertures in the plate 34.

The operation and use of the spine plate assembly or spine repair device 32 of the present invention is described with respect to spine plate 34 having bushings 36 therein and having a plurality of apertures 61, 63, 67 and 69 and inclined threaded holes 65 and 71 formed therein. Bushing 36 may be inserted into spine plate 34 in the manner described either before delivery of the spine plate assembly to the sight of operation or immediately prior to the procedure. Spine plate 34 is attached to targeting device or jig 234 that allows for insertion of the spine plate 34 in a percutaneous manner and allows a bone drill 236 and bone screws 38 to be directed to engage the spine plate via a percutaneous technique.

Figure 14:
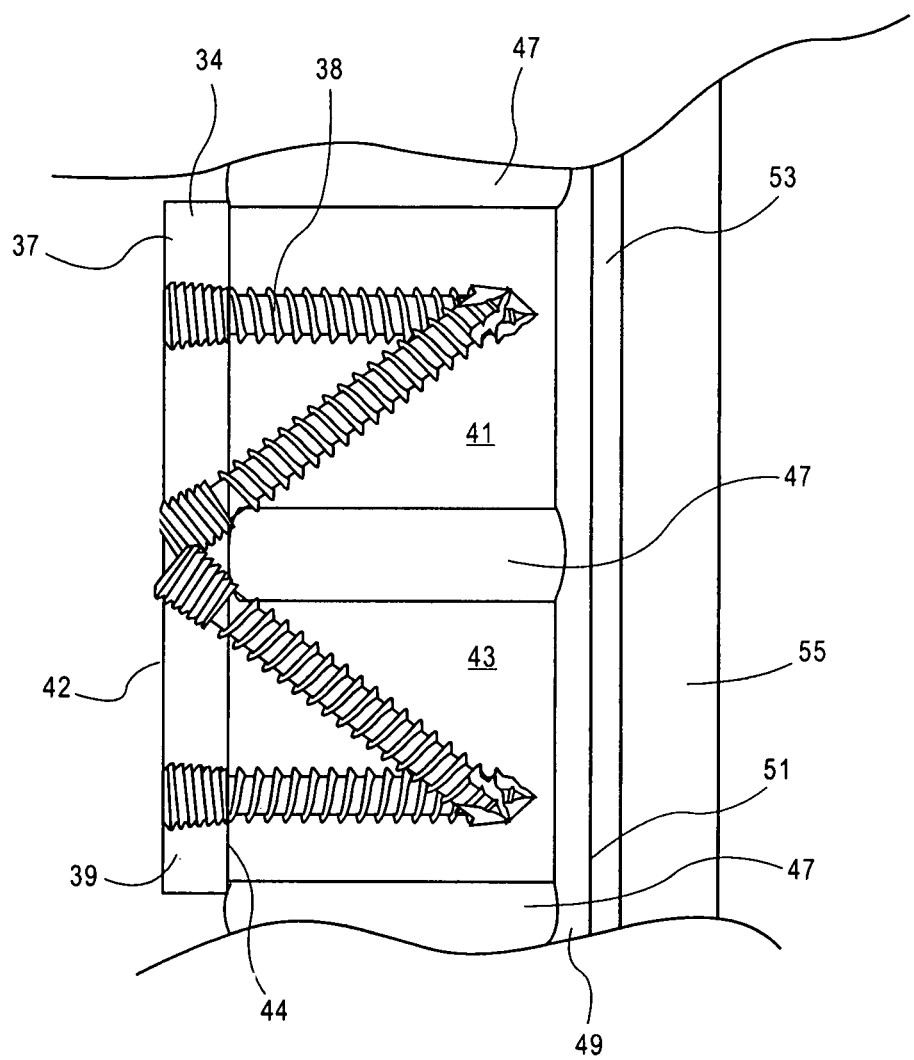
FIG. 14 is a side elevational view of the spine plate of FIG. 1 secured to a plurality of vertebral portions of a spine of a mammalian body.

For treatment of the spine, static spine plate 34 is located above first and second vertebral bodies and subsequently attached (see FIG. 14). As is known, the anatomy of the spine contains intervertebral discs 47 separated by vertebral bodies 41, 43, and includes a posterior longitudinal ligament 49, dura 51, an area of cerebro-spinal fluid 53 and spinal cord 55. More specifically, once an incision is made in the surrounding tissue, the spine plate 34 may be attached. In this process, the plate 34 having bushings 36 seated therein may be positioned over the first and second vertebral bodies. Pins are then inserted into anchoring holes 110 in the spine plate 34 and into the vertebral bodies. These pins (not shown) are preferably small threaded wire used to retain the spine plate 34 in position prior to and while the bone screws 38 are secured to the vertebral bodies through the plate 34. Following placement of the plate 34 and initial attachment using the attachment pins, the targeting jig 234 is attached to the spine plate 34 by the threaded engagement of the pivot bolt 252 with the receptor 72 on the spine plate 34. The pivot bolt 252 is secured on the attachment plate 238 of the jig 234 and aligned so as to align the targeting apertures 240, 242, 244 in the plate 34 of the jig 234 with the respective openings 61 and 65 in the spine plate 34 and first end portion 37 of the spine plate 34. Location pin 254 may be inserted through the appropriate aperture 250 in order to align the targeting device 234 with the spine plate 34. Once positioned, drilling sleeves 246 are inserted into openings in the jig 234, and drill 236 is used to form pilot holes in the respective locations. More specifically, openings or pilot holes are drilled in the first vertebral body through the targeting openings 240, 242, 244 and through first 61, second 63 and third holes 65 in spine plate 34. Subsequently, screws 38 are inserted into the respective openings and rotationally threaded into bushings 36 and inclined aperture 65 and into the first vertebral body. First, the variable angle bone screws are inserted through bushings 36 followed by oblique angled or inclined screws into inclined apertures 65. Following the insertion of first three screws, the pivot bolt 252 is loosened, location pin 254 is removed, and the jig 234 is rotated 180 degrees and then re-secured or tightened to plate 34 and location pin 254 is inserted. The remaining holes four 67, five 69 and six 71 are both drilled and screws attached according to the same method. One or more bone screws 38 having a threaded head 224 or a non-threaded head may be placed into the spine plate 34 as needed. Once the spine plate 34 is attached, the targeting jig 234 and pins may be removed as desired and the incision may be closed. The plate 34, in its attached position, as shown in FIG. 14, may be positioned against the bone, or vertebral bodies 41, 43, or may be spaced a distance from the vertebral bodies due to the angular stability created by the screws 38 relative to the plate 34, such as, but not limited to a distance of one to two millimeters away from the bone.

In one suitable procedure, before complete insertion of a bone screw 38 into a bushing 36 or 171 disposed in aperture formed with a circumferential groove 176 therein, for example apertures 172 and 174 located in the spine plate 34, the bushing 36 is rotated within the aperture until pivot axis 170 of the bushing 171 is in a desired location in the plane of the spine plate 34. Such rotation is guided by the travel of the first and second wings 156, 158 in groove 176. Once in position, upper and lower planar surfaces 181, 184 within the spine plate 34 limit the pivotal movement of the bushing 36 within the spine plate 34. In this manner, the bushing 36 can rotate 360 degrees within spine plate 34 to allow for the screw 38 to be inserted into the bone in any desired direction.

When a bone screw 38 is threaded into bushing 36, the travel of the screw 38 through the tapered threaded bore 128 of the bushing 36 causes the annular wall 130 of the bushing 36 to radially expand so that the outer surface 130 of the bushing 36 is fully engaged and in compression by internal surface 157 of the spine plate 34. The slit 132 in the bushing 36 permits the radial expansion of the bushing 36. The complete recessing of bushing 36 within the aperture 61, specifically the complete concentric engagement of outer bushing surface 130 by internal surface 157 of the spine plate 34, enhances the rigid fixation of the bushing 36 within the spine plate 34. In this manner, bushing 36 is affixed rigidly into aperture 61 of the spine plate 34 by the fastening of bone screw 38 into the spine plate 34 and the underlying vertebral body of the mammalian body being treated. The increased friction between the bushing 36 outer surface and spine plate 34 internal surface 157 further increases the resistance to motion of the screw-bushing-plate assembly in all directions when the screw 38 is fully seated in the plate 34 and underlying vertebral body.

A drive socket 228 can be utilized with a drive element (not shown) for moving the bone screw 38 longitudinally relative to spine plate 34, for example, for advancing or retracting the screw 38 relative to the spine plate 34 throughout the procedure.

It is noted that while specific embodiments are described for use with screws inserted into four bushings and two inclined openings, variations on the number of screws and apertures would not depart from the overall purposes of the embodiments disclosed.

A spine repair assembly 32 according to the foregoing is easy to attach and capable of locking the bone screw 38 and plate 34, provides for a variable angle of attachment and has increased rigidity within the vertebral body. The static cervical spine plate 34 attached according the foregoing method has at least three fixation screws 38 for each one of the vertebral bodies extending into the vertebral body at different angles. The first and second inclined apertures 65 and 71 are further provided in an inclined orientation relative to the plate-like member or body 40 so as to enhance securement of the first and second end portions 37, 39 to the first and second vertebral portions 41 and 43 when bone screws 38 are introduced through the threaded apertures or screw holes into the vertebral portions. The static cervical spine plate 34 thereby provides a multi-planar fixation of the vertebral body allowing a stronger construct attaching the plate to the vertebral body. This provides a significant advantage over currently available plates which only permit the insertion of two screws per vertebral body within the same angular orientation or which are co-planar.

Figure 15:
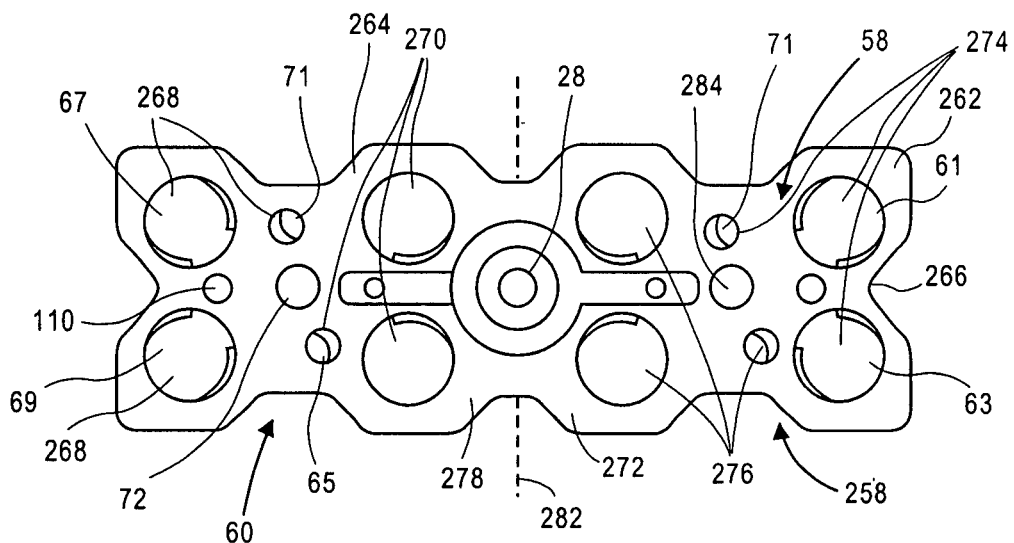
FIG. 15 is a bottom plan view of another embodiment of a spine plate of the present invention with the bushings and screws removed.

In a further embodiment of the static cervical spine plate of the present invention, as illustrated in FIG. 15, a longitudinally-extended spine plate 258 is provided to treat a mammalian body having adjacent first and second vertebral portions 41 and 43 separated by a reconstructed region 260, such as a bone graft or implant, from adjacent third and fourth vertebral portions 261 and 263 in a spine. The static cervical spine plate 258 contains substantially similar elements to static cervical spine plate 34 and like reference numerals have been used to illustrate like elements of cervical spine plate 258. The spine plate 258 comprises an elongate plate-like member 262 that has a first end portion 264 adapted for fastening to the first and second vertebral portions and a length sufficient to extend over the first and second vertebral portions. The first end portion 264 is further provided with first and second sets 268 and 270 of longitudinally spaced apart threaded screw holes for use with bone screws 38 to secure the elongate plate-like member 262 respectively to the first and second vertebral portions. More specifically, the first set of screw holes preferably comprises first, second and third screw holes 61, 63, 65 formed by first and second apertures 61, 63 with bushings 36 seated therein and inclined aperture 65. The second set of screw holes preferably comprises fourth, fifth and sixth screw holes 67, 69, 71 formed by first and second apertures 61, 63 with bushings 36 seated therein and inclined aperture 65. The second end portion 272 has a length sufficient to extend over the third and fourth vertebral portions and is provided with third and fourth sets 274 and 276 of longitudinally spaced apart threaded screw holes for use with bone screws 38 to secure the elongate plate-like member 262 respectively to the third and fourth vertebral portions. The third and fourth sets 274 and 276 of longitudinally spaced apart threaded screw holes are comprised of substantially similar arrays of screw holes as provided in first and second sets 268 and 270, and like reference numbers are used to illustrate like components.

The four vertebral portions 41, 43, 261, 263 of the spine may be directly adjacent to each other. Alternatively, plate 258 may vary in size, so that a central portion 278 may be provided between the first end portion 264 and the second end portion 272 of varying length to accommodate a spacing between vertebral sections or nonadjacent sections. Central portion 278 may be used to attach the respective first end 264 and second end 272 of the spine plate 258 so as to extend over a graft 260 or other insert between the first and second vertebral portions 41 and 43 and the third and fourth vertebral portions 261 and 263. The central portion 278, as illustrated in FIG. 15, may be provided with a centralized opening 280 or aperture which may be used for example in viewing the graft 260 being attached, or for the insertion of a screw 38 to retain the graft 260 in place on the plate 258.

Spine plate 258 may further include a plurality of recesses 60 surrounding its outside edge in one or more of the first, second, third and fourth side surfaces 48, 50, 52, 54, or may comprise a substantially planar surface for each side surface. In addition, substantially similar to spine plate 34, spine plate 258 is contoured to conform with the vertebral bodies onto which it is placed. That is, inner surface 44 of the first end portion 264 and the second end portion 272 is concave, while outer surface 42 is convex. Central portion 278 may likewise be concave. Furthermore, first end portion 264 and second end portion 272 include a degree of concavity between the first end 264 and the second end 266.

A first threaded receptor 72 for the pivot bolt 252 of the jig 234 is centralized along centerline 282 within the first end portion 264 of spine plate. This threaded receptor 72 is flanked on each side by anchoring holes 110 for receipt of an anchoring device. Second end portion 272, likewise, has second pivot bolt receptor 284 equivalent to first threaded receptor 72 and anchoring holes 110 or openings in an array substantially similar to the first end portion 264 for attachment of the jig 234.

Jig 234, substantially as described herein and illustrated in FIGS. 12 and 13, may be used for attachment of static cervical spine plate 258. In this embodiment, a single jig 234 may be used, so as to attach the first end 264 of the spine plate 258 at the first pivot bolt receptor 72, and subsequently removed and attached at second pivot bolt receptor 284 so as to be secured to the second end 272 of the spine plate. Alternatively, a pair of jigs 234 may be used for the attachment of the spine plate 258.

The operation, attachment, and use of the static cervical spine plate 258 are substantially as described with respect to spine plate 34. In the present embodiment, spine plate 258 is attached to first and second vertebral bodies and third and fourth vertebral bodies. In this process, the surgical procedure, prior to attachment of the elongate plate 258 may include, first removing one or more vertebral bodies from the spine using known procedures. Subsequently, a graft 260 may be taken and cut to size to conform with the appropriate dimensions needed for insertion in place of the removed vertebral body. Once the graft 260 is in place, the plate 258 may be positioned over the first and second vertebral bodies, the graft 260, and the third and fourth vertebral bodies. Pins are then inserted into anchoring holes 110 in the first end 264 of the spine plate 258 and into the vertebral bodies. Pins may also be inserted into the anchoring holes 110 in the second end 272 of the spine plate 258 and into the vertebral body. Following placement of the plate 258 and initial attachment using the attachment pins, the targeting jig 234 is attached to the first end 264 or the second end 383 of the spine plate 258 by the threaded engagement of the pivot bolt 252 into the receptor 72 or 284 on the spine plate. The plate 238 of the jig 234 is aligned so as to align the targeting apertures 240, 242, 244 in the plate 238 with the respective openings 61 and 65 in the spine plate 258. The pivot bolt 252 is then secured and location pin 254 may be attached. Openings are then drilled in the vertebral bodies through the targeting openings 240, 242, 244, and subsequently the screws 38 are inserted into the respective openings as described with respect to spine plate 34. Following the insertion of the screws, the pivot bolt 252 is loosened, the jig 234 is rotated 180 degrees and re-secured and both the remaining holes are drilled and screws attached according to the foregoing method. During the process of attachment, the graft 260, if applicable, may be viewed through the central opening 280 in the spine plate 258, and may be further attached to the spine plate 258 using a screw, if necessary or desired.

If a single jig 234 is used, following the attachment of screws in the first end of elongate body, the jig 234 may be disconnected from plate 258 and attached to the second or lower end portion 272 of the spine plate 258 at the pivot bolt receptor 284. Openings are drilled and bone screws 38 are subsequently rotationally inserted in the same manner as provided for the first end portion 264 of the plate. Once the spine plate 258 is completely attached, the targeting jig 234 is removed. Pins may be removed as desired and the incision may be closed.

Similar to static cervical spine plate 34, spine plate 258 attached according the foregoing method has at least three fixation screws 38 for each one of four vertebral bodies extending into the vertebral body at different angles, allowing a stronger construct attaching the plate 258 to the vertebral body. Moreover, the spine plate 258 can be sized to accommodate attachment in the event of removal of a vertebral body and/or grafting between respective pairs of vertebral bodies.

In a further preferred embodiment, the cervical spine plate may be dynamic. As illustrated in FIGS. 16-18 and 24-30, dynamic cervical spine plate 286 has a first end portion 264 and a second end portion 272 substantially similar to the first end portion 264 and second end portion 272 of static spine plate 286, shown in FIG. 15, and have been described in detail with reference to spine plates 34 and 258. Like reference numerals have been used to illustrate like elements of dynamic cervical spine plate 286. As with spine plate 258, spine plate 286 is contoured to conform with the vertebral bodies onto which it is placed, and first end portion 264 and second end portion 272 include a degree of curvature extending from the first end to the second end. Spine plate 286 may, likewise, include a plurality of recesses 60 surrounding its outer surfaces 48, 50, 52, 54 similar to spine plates 34 and 258.

In addition to first end portion 264 and second end portion 272 which respectively carry first and second sets 268 and 270 of screw holes and third and fourth sets 274 and 276 of screw holes, as well as jig and anchoring attachment bores 72, 284 and 110, dynamic cervical spine plate 286 further includes a telescoping central portion 288 between the first and second end portions 264 and 272, permitting adjustment of the longitudinal spacing between the first and second end portions. In one preferred embodiment, the longitudinal spacing between first and second telescoping sections can be increased by a maximum of five millimeters. However, it is understood that variations in spacing from 1 mm to 20 mm are acceptable for the purposes provided. Telescoping central portion 288 includes first and second telescoping sections 290 and 292 and may include a locking assembly 294 for fixing the longitudinal spacing between the first and second end portions 264, 272. First telescoping section 290 includes spaced-apart first and second rails 296 and 298 that extend longitudinally from the first end portion 264 of the spine plate 286. First telescoping section 290 may comprise a thickness corresponding to the thickness of spine plate 286, and may be of any suitable length. First telescoping section 290, in one preferred embodiment, includes a first recess 302, slit or guide member on an inner side surface 304 of first rail 296 and a second recess 306, slit or guide member on inner side surface 308 of second rail 298 for insertion of a correspondingly shaped ridge. Preferably, first recess 302 and second recess 306 extend longitudinally along a length of the first rail 296 and second rail 298, respectively. Second telescoping section 292 includes a slide member 310 extending longitudinally from the second end portion 272 of the spine plate 286 for slidable disposition between the first and second rails 296 and 298. Second telescoping section 292 may comprise a thickness corresponding to the thickness of spine plate 286, and may be of any suitable length, but is preferably of a length corresponding to the length of first telescoping section 290. Second telescoping section 292 may have on a first outer side surface 312 a first ridge 314 or guide surface shaped to be received in the first recess 302, and may have on a second outer side surface 316 a second ridge 318 or guide surface shaped to be received in the second recess 306, thereby permitting the telescopic engagement of the first telescopic section 290 and the second telescopic section 292.

Figure 29:
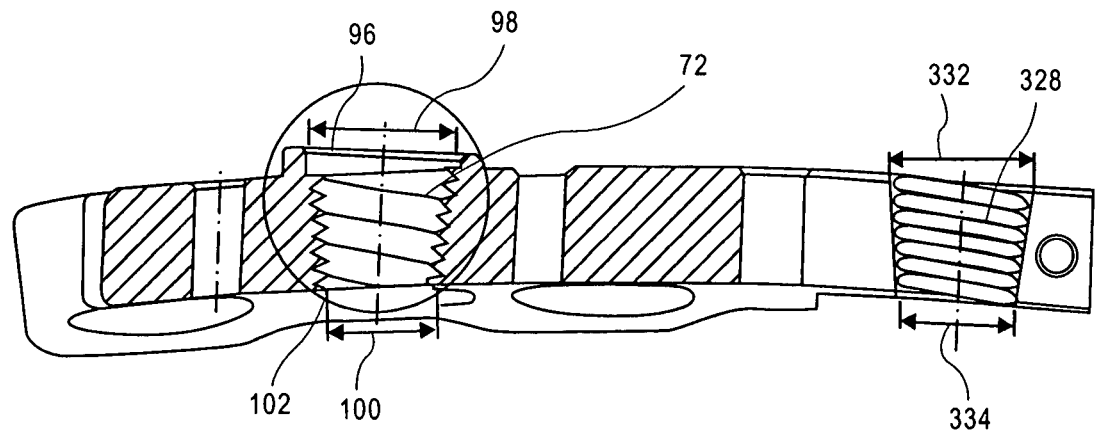
FIG. 29 is a cross-sectional view of the second portion of the spine plate of FIG. 27 taken along the line 29-29 of FIG. 27.
Figure 30:
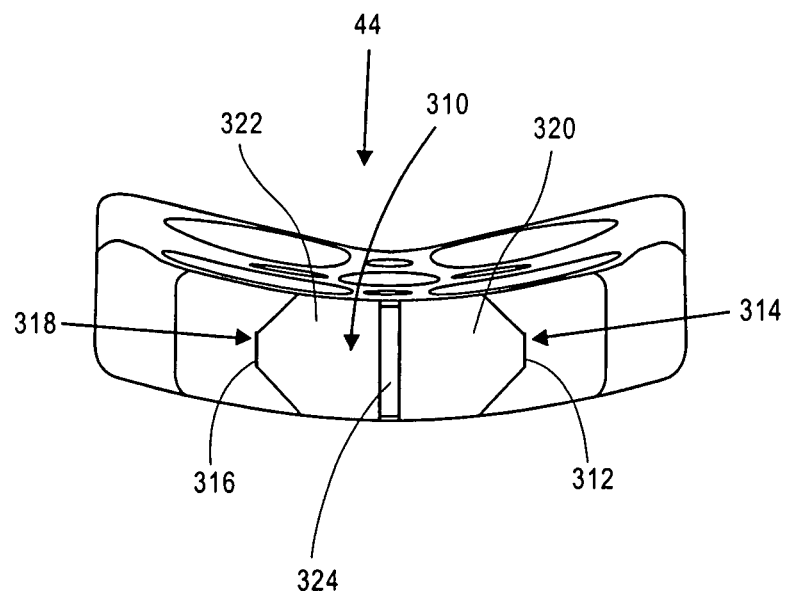
FIG. 30 is an end elevational view of the second portion of the spine plate of FIG. 27 taken along the line 30-30 of FIG. 27.

Locking assembly 294 is formed in telescoping central portion 288 and includes spaced-apart first and second arms 320 and 322 in slide member 310. Slide member 310 is provided with a longitudinally-extending slit 324 between the first and second arms 320, 322. A locking element 326 is extendable into the slit 324 for urging the first and second arms 320, 322 laterally against the respective first and second rails 296 and 298, thereby longitudinally locking the slide member 310 between the first and second rails 296 and 298. More specifically, a threaded bore 328 is provided in slide member 310, extending into a portion of first arm 320 and second arm 322, and across slit 324. Threaded bore 328 receives the threaded locking element 326 or fixation device, which may receive a threaded screw 326 or any other suitable threaded element. Screw 326 preferably has an outer diameter 330 along a portion thereof that is greater than the diameter of threaded bore 328, so that the rotational insertion of screw 326 into threaded bore 328 urges first and second arms 320, 322 laterally apart and presses arms against respective first and second rails 296 and 298. As a result, the telescoping central portion 288 is frictionally locked in position. In one preferred embodiment, as illustrated in FIG. 29, threaded bore 328 tapers from a first outer diameter 332 to a narrower inner diameter 334. Screw 326 may have a uniform outer diameter 330 and preferably has a length at least equivalent to the thickness or depth of threaded bore 328. Screw 326 may further include a tool engagement portion or head 336 for receipt of a tool, such as a hex key receptor. The uniform diameter screw 326 forces the arms carrying the tapered bore 328 outward. Alternatively, screw 326 may have a tapered shaft. Screw 326 can be similar to screw 38 and have a threaded head 224 with a diameter greater than the shaft 202 for use in association with the locking assembly 294 in instances in which a graft 260 or other implant is used. Likewise, while a threaded bore 328 and threaded screw 326 are specifically described, it is understood that alternative bores and locking elements may be acceptable for the purposes provided, such as an un-threaded bore or element. Moreover, while a single threaded bore for receipt of a single screw 326 is specifically illustrated, a plurality of locking elements 326 may be included in the locking assembly 294.

Figure 18:
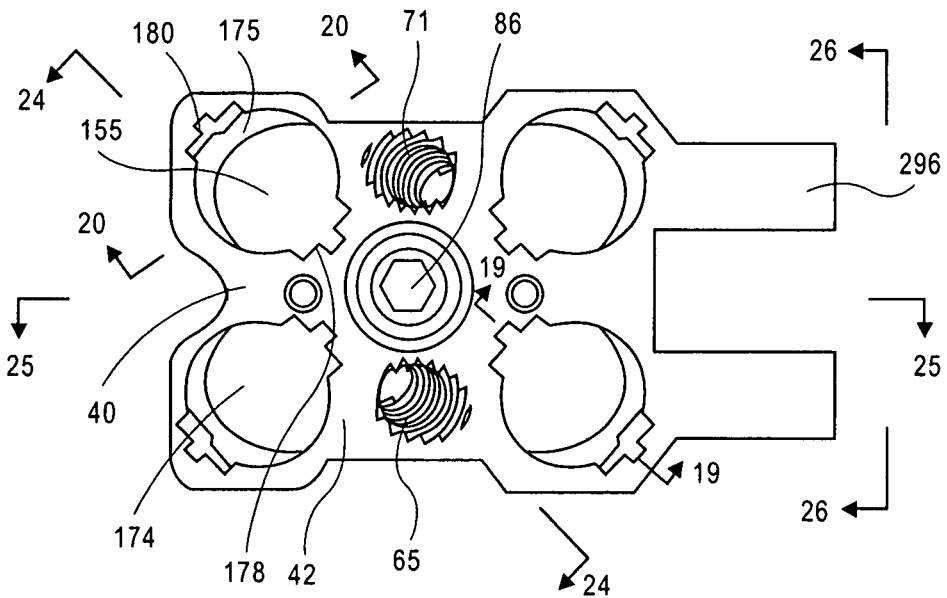
FIG. 18 is a top plan view, with the bushings and bone screws removed, of a first portion of the spine plate of FIG. 16 taken along the line 18-18 of FIG. 17.

An embodiment of the bore of aperture 174 is formed with an internal surface 175, shown in FIGS. 18-20, that is centered on the vertical centerline 155 of the aperture 174 and is arcuate and preferably concave relative to the centerline 155. More preferably, the arcuate shape of surface 175 approximates the arcuate shape of bushing outer surface 130. Body 40 is provided with a circumferentially-extending ridge 159, 161 around each of the upper and lower ends of the aperture 174 adjacent respective outer and inner faces 42 and 44 of the body 40. A niche, gap, slit or slot 178 or 180 extends through outer face 42 of the spine plate 34 on opposite sides of the entrance of aperture 174. Such first and second slots 178 and 180 are sized to receive respective first and second wings 156 and 158 when bushing 171 is disposed in a vertical position with respect to the aperture 172. The slots 178 and 180 serve as entrances to respective first and second internal recesses 134 and 136 extending through at least a portion of internal surface 175 at opposite sides of aperture. Each such recess is formed with a bottom surface that is part of a ramped, arcuate lower surface 168 extending upwardly and inwardly from the bottom of the recess. A similar ramped, arcuate upper surface 166 is diametrically opposed to surface 168 for forming a portion of the other side of the recess. The lower and upper ramped surfaces 166 and 168 end at respective upper and lower shoulders 146 and 148, which have respective upper and lower limiting surfaces 150 and 152 that extend parallel to horizontal centerline 126 of the portion of the spine plate 34 in the vicinity of the aperture 174 (See FIG. 20). Alternatively, or in addition, outer face 42 of the spine plate 34 can be punched at the entrance of first and second slots of 178 and 180 to similarly restrict removal of the bushing from body 40.

As described more fully in U.S. patent application Ser. No. 11/588,037, any or all of apertures for the bushing 171 can include a groove (not shown) extending at least partially about the vertical centerline 155 of the aperture and preferably entirely around the circumference of the aperture. The groove extends in the plane of the portion of the body 40 in the vicinity of the aperture and is preferably formed with an upper surface coplanar with upper limiting surface 182 and a lower surface coplanar with lower limiting surface 186. The planar upper and lower surfaces extend parallel to each other.

Bushing 171 is inserted into aperture 174 in the same manner discussed above with respect to the insertion of the bushing 36 into aperture 61. The bushing 171 is initially placed in a vertical position relative to the body 40 and first and second wings 156 and 158 of the bushing aligned with first and second slots 178 and 180 of the spine plate. The bushing 171 is then vertically inserted into the aperture 174, with the vertically aligned wings 156 and 158 traveling through respective slots 178 and 180 into respective recesses 134 and 136. The leading edge or winged portion 162 of each wing 156 and 158 engages bottom surface 140 of the recess to limit the insertion travel of the bushing. Thereafter, the bushing 171 is rotated about a pivot axis 170 that extends horizontally through the bushing and the centers of first and second wings 156 and 158. During such rotation, the leading winged portion 162 of each of the wings 156 and 158 travels along the lower ramped surface 142 forming first and second recesses 134 and 136.

Once the bushing has been rotated to a horizontal position relative to the body 40, the bushing can be rotated within aperture 174 about an axis extending perpendicular to the plane of the spine plate so that the diametrically-aligned wings 156 and 158 of the bushing are in the desired portions of annular groove 176. Such portions of the groove 176 serve as transversely-aligned or diametrically-aligned recesses for receiving the wings 156 and 158. Upper and lower internal surfaces 183 and 185 of the spine plate can serve as limiting surfaces, like limiting surfaces 150 and 152, for limiting the range of pivotal motion of the bushing 36 about the pivot axis 170.

A jig 234 substantially as described herein and illustrated in FIGS. 12 and 13 may be used for attachment of dynamic cervical spine plate 286. In this embodiment, a single jig 234 may be used, so as to attach the first end of the spine plate 286 to the first pivot bolt receptor 72, and subsequently removed and attached to second pivot bolt receptor 284 so as to be secured to the second end of the spine plate. Alternatively, a pair of jigs 234 may be used for the attachment of the spine plate.

Figure 31:
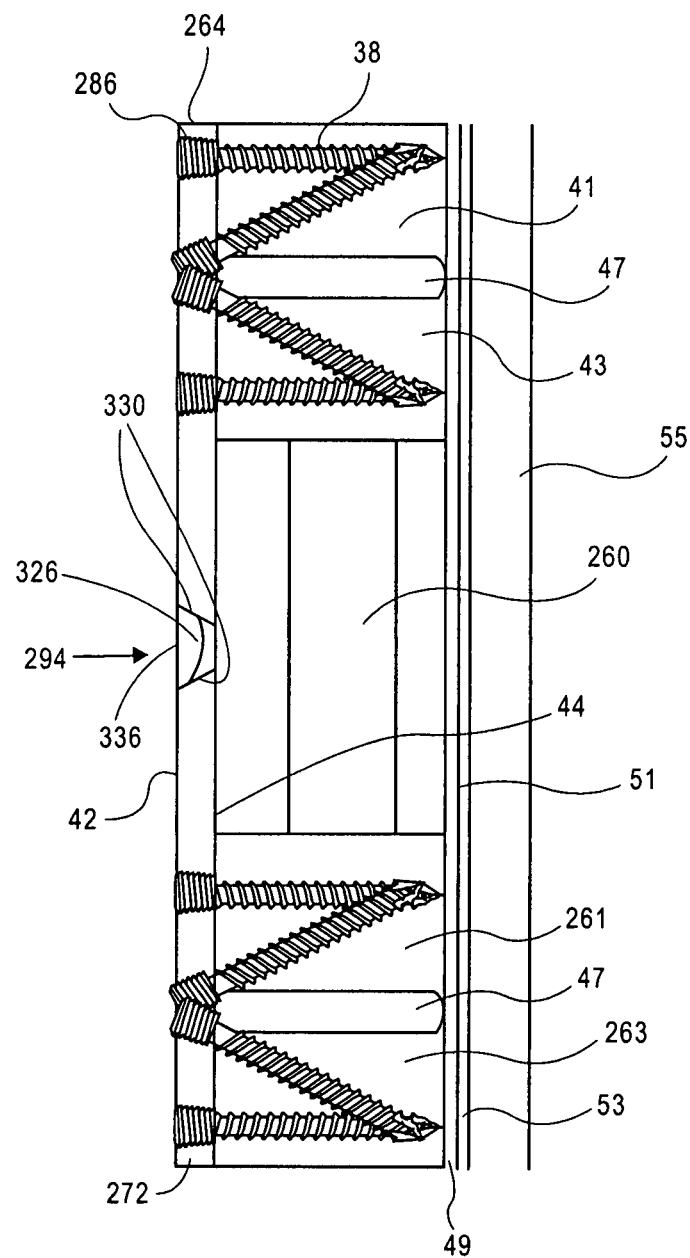
FIG. 31 is a side elevational view of the spine plate of FIG. 16 secured to a plurality of vertebral portions of a spine of a mammalian body.

In the method and operation of use of the dynamic spine plate 286, the spine plate 286 may be attached to first and second vertebral bodies and third and fourth vertebral bodies as set forth with respect to static spine plate 286 (see FIG. 31). The plate 286, in its attached position, as shown in FIG. 31, may be positioned against the bone, or vertebral bodies 41, 43, 261, 263 or may be spaced a distance from the vertebral bodies, due to the angular stability created by the screws 38 relative to the plate 286, such as, but not limited to a distance of one to two millimeters away from the bone. Dynamic spine plate 286 further includes telescopic central portion 288 which may be telescopically expanded or contracted to accommodate larger or narrower spaces between the first and second vertebral bodies and the third and fourth vertebral bodies. More specifically, once the spine plate 286 is telescopically adjusted and subsequently attached to the first and second vertebral bodies and the third and fourth vertebral bodies using the foregoing method, an external device (not shown) may be used to compress the plate. Alternatively, an external device may not be needed if an allowed range of compression is warranted. Threaded locking element 326 or fixation device is then rotationally inserted into tapered threaded bore from outer surface 42 to vertebrate facing surface 44 using a tool, such as a hex key. The rotational insertion of locking element 326 into tapered threaded bore 328 forces first and second arms 320, 322 of slide 310 apart, frictionally engaging the outer side surfaces 312, 316 of first and second arms 320, 322 with respective inner surfaces 304, 308 of first and second rails 296 and 298, thereby locking the telescopic central portion 288 in position and locking the locking assembly 294. In one preferred method of operation, when screw 38 is used in place of locking element 326, screw 38 may be inserted into threaded bore and into an adjacent graft 260 or implant seated below the plate 286.

The dynamic spine plate 286 used according to the foregoing method includes both the advantages of the static spine plate 286 and the capability of dynamic adjustment for variations in spacing between the pairs of vertebral bodies.

Figure 32:
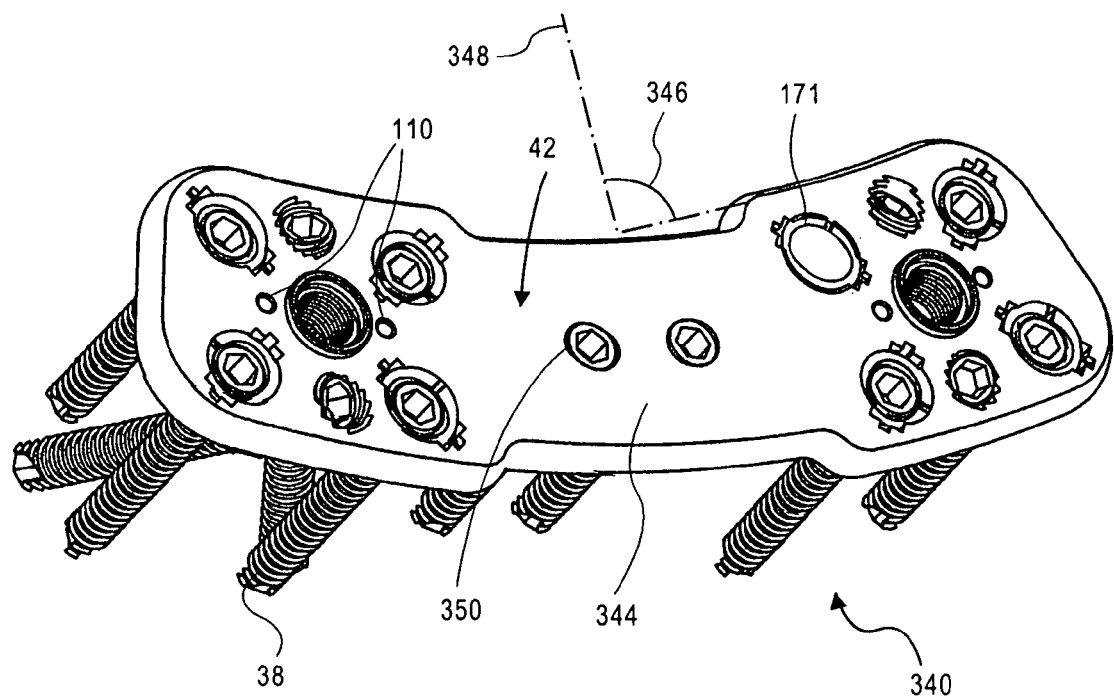
FIG. 32 is a top perspective view of a yet another embodiment of a spine plate of the present invention with a plurality of bone screws disposed therein.
Figure 33:
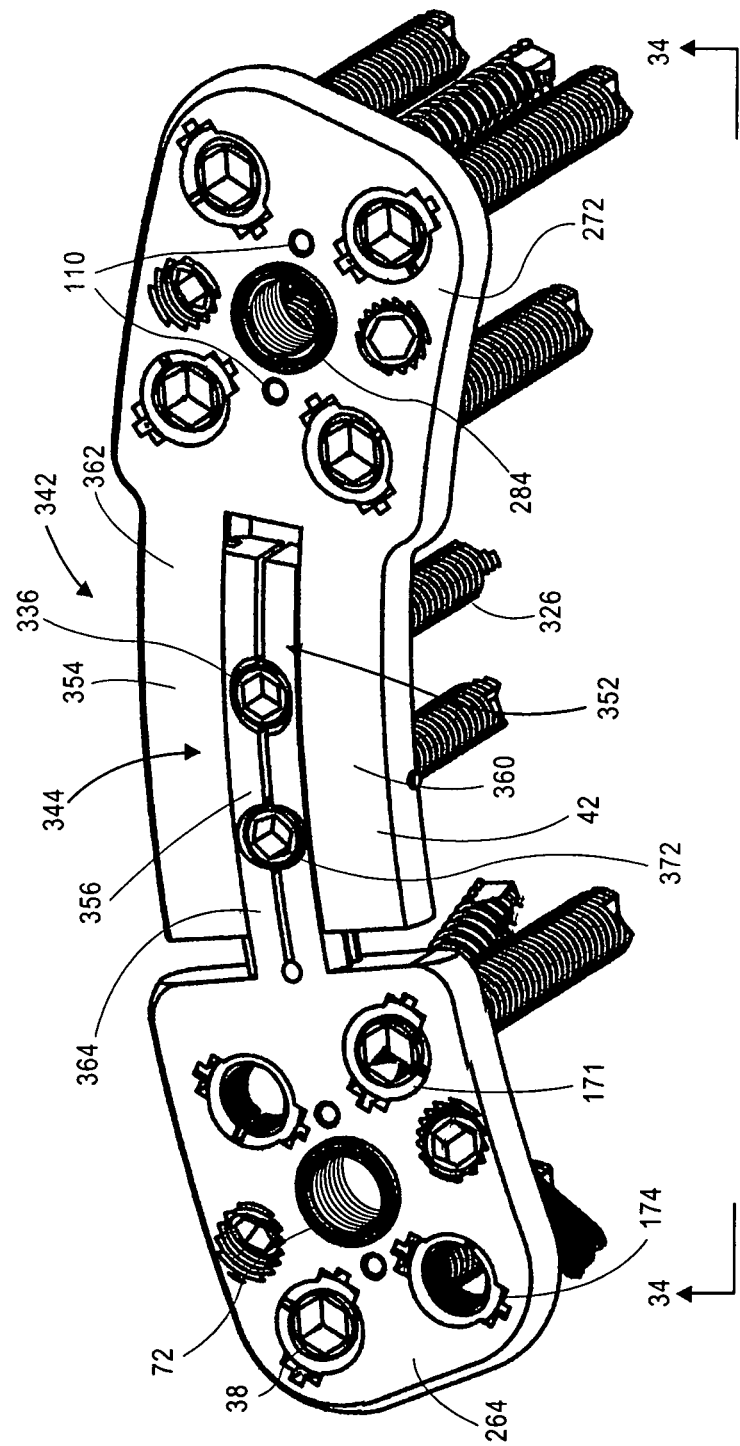
FIG. 33 is a top perspective view of a yet further embodiment of a spine plate of the present invention with a plurality of bone screws disposed therein.
Figure 34:
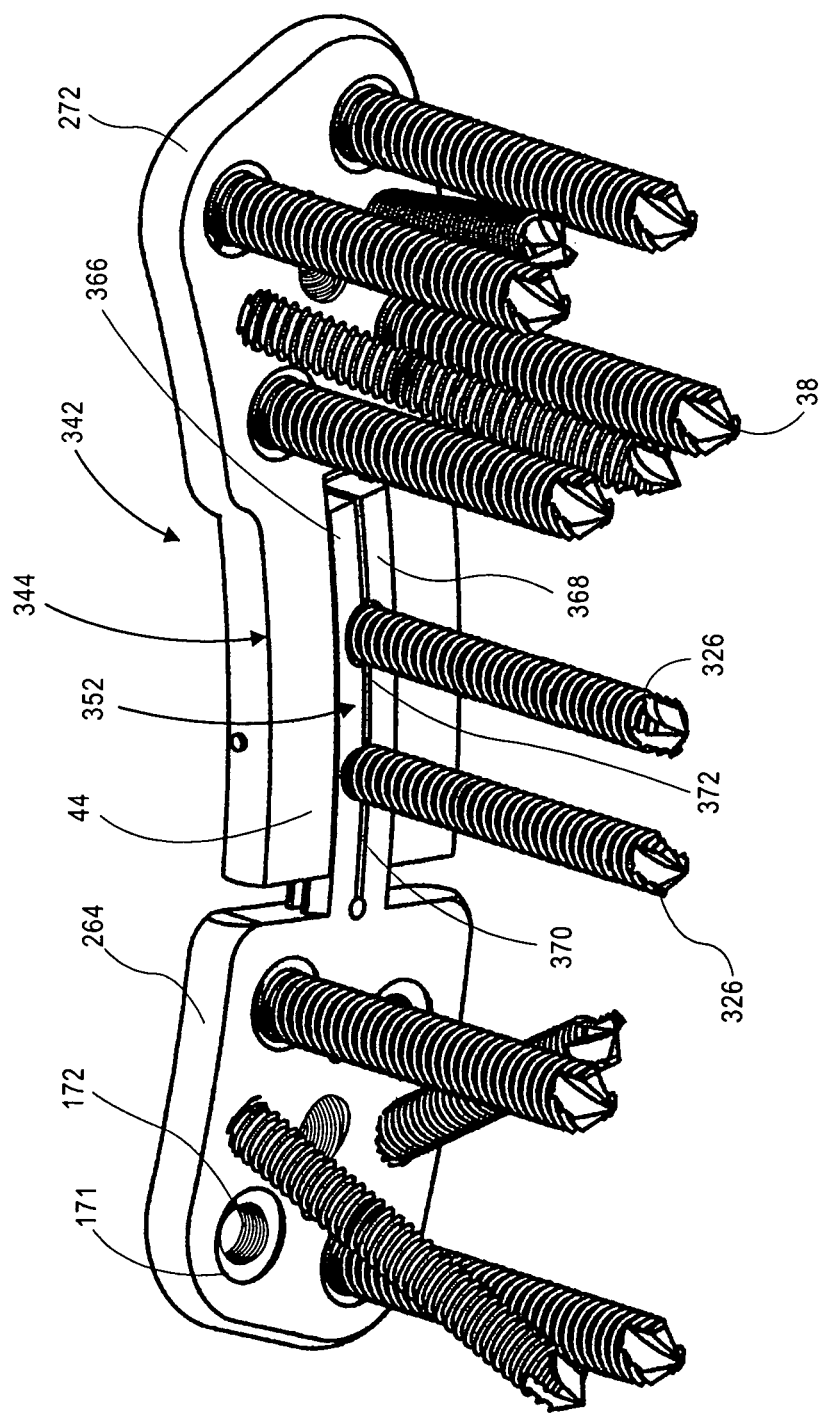
FIG. 34 is a bottom perspective view of the spine plate of FIG. 33 taken along the line 34-34 of FIG. 33.

A further preferred embodiment is represented by thoraco lumbar plate 340 or 342, as illustrated in FIGS. 32-34. Thoraco-lumbar plate 340 may be static (FIG. 32) or the plate 342 may be dynamic (FIGS. 33-34). Thoraco-lumbar plates 340, 342 have a first end portion 264 and a second end portion 272 substantially similar to the first end portion 264 and second end portion 272 of spine plates 258 and 286, and like reference numerals have been used to illustrate like elements of thoraco-lumbar plate 340 and 342. As with spine plates 258 and 286, thoraco-lumbar plate 340 and 342 have a first end portion 264 with first and second sets 268 and 270 of screw holes for receipt of bone screws 38 including apertures 61, 172 or 174 for receipt of bushing 36 or 171 and inclined threaded apertures 65, 71 for receipt of a threaded screw. Additionally, first end portion 264 and second end portion 272 each include a threaded tool receptor 72, 284 for receipt of the pivot bolt 252 centralized within the end portion and flanked by first and second anchoring holes 110.

Thoraco-lumbar plates 340 and 342 further include a curved central portion 288 having a length separating the first end portion 264 from the second end portion 272. Curved central portion 344 of thoraco-lumbar plate 340 and 342 have a curvature or geometry that permits the attachment of the plate in the proper position in the mammalian body. In this regard, thoraco-lumbar plate 340, 342 is attached to a side of the spinal vertebral bodies. In this location, the spine includes a curvature. Accordingly, curved central portion 344 positions the first end portion 264 and second end portion 272 of plate 340 or 342 at respective first and second vertebral bodies and third and fourth vertebral bodies so as to attach to different levels of the spine. The curvature of the central portion 344 and the length of central portion 344 may vary to accommodate attachment to adjacent vertebral bodies, or vertebral bodies spaced a distance apart. For instance, a thoraco-lumbar plate 340 or 342 may be provided having a curved central portion 344 with a length equivalent to the distance of one or more vertebral bodies, so that the first end portion 264 may be spaced from the second end portion 272. A graft 260 may be inserted between the vertebral bodies attached to the respective end portions. In a preferred embodiment the degree 346 of curvature of central portion 344 is approximately 28 degrees, centered over centerline 348, extending through the center of curved central portion 344. Curved central portion 344 may also include one or more bores or threaded bores 350 for receipt of a fastening device, such as a threaded screw 38, or for purposes of viewing through the plate 340 while attaching to the vertebral bodies and/or graft 260. Fastening device or threaded bone screw 38 may be used to secure the graft 260 to the plate 340 or 342 at the central portion 344.

Alternatively, curved central portion 344 may be provided with a telescoping portion 352, as illustrated in FIGS. 33 and 34, to permit the dynamic adjustment of the overall length of thoraco-lumbar plate 342. The telescoping portion 352 of thoraco-lumbar plate 342 has first and second telescoping sections 354 and 356 and may include a locking assembly 358 for fixing the longitudinal spacing between the first and second end portions 264, 272 similar to dynamic cervical spine plate 286. As with cervical spine plate 286, first telescoping section 354 includes spaced-apart first and second rail 360 and 362 that extend longitudinally from the first end portion 264 of the spine plate, but first and second rails 360 and 362 of thoraco-lumbar plate 342 further include a degree of curvature. More specifically, first rail 360 and second rail 362 have an equal degree of curvature corresponding to static thoraco-lumbar plate 340. The specific degree of curvature may vary depending upon the patient and purposes for which the thoraco-lumbar plate 342 is used. Second telescoping section 356 includes slide member 364 extending longitudinally from the second end portion 272 of the spine plate 342 and includes an equivalent and corresponding degree of curvature for slidable disposition between the first and second rails 360 and 362. First telescoping section 354 and second telescoping section 356 each have a thickness corresponding to the thickness of thoraco-lumbar plate 342, and may be of any suitable length. Like the dynamic cervical spine plate 286, first telescoping section 354, in one preferred embodiment, includes a first recess 302 on an inner side surface 304 of first rail 360 and a second recess 306 on inner side surface 304 of second rail 362 for insertion of correspondingly shaped ridges 314 and 318 respectively on a first outer side surface 312 and a second outer side surface, permitting the telescopic engagement of the first telescopic section 354 and the second telescopic section 356. Locking assembly 358 is similarly formed in telescoping central portion 352 and includes spaced-apart first and second arms 366, 368 and a longitudinally-extending slit 370 between the first and second arms 366, 368. Locking element 326 or fixation device may be provided extendable into the slit 370 for urging the first and second arms 366, 368 laterally against the respective first and second rails 360 and 362, thereby longitudinally locking the slide member 364 between the first and second rails 360 and 362. More specifically, at least one, but preferably two or more longitudinally spaced apart threaded bores 372 are provided in slide member 364, extending into a portion of first arm 366 and second arm 368, and across slit 370. Threaded bores 372 receive a threaded locking element 326 as has been described with respect to dynamic cervical spine plate 286. In the preferred embodiment, and as illustrated in FIGS. 33-34, threaded locking element 326 is bone screw 38 capable of both securing a graft 260 or other implant to the thoraco-lumbar plate 342 and locking the dynamic telescoping assembly to prevent separation of the first end portion 264 and the second end portion 272. The rotational insertion of locking element 326 into a threaded bore 372 urges first and second arms 366, 368 laterally apart and presses arms against respective first and second rails 360 and 362, frictionally locking the first end portion 264 and second end portion 272 in position. While a threaded bore 372 and threaded locking element 326 are specifically described, it is understood that alternative bores and locking elements may be acceptable for the purposes provided, such as an un-threaded bore or element.

A jig 234 substantially as described herein and illustrated in FIGS. 12 and 13 may be used for attachment of thoraco-lumbar plates 340 and 342. In this embodiment, a single jig 234 may be used, so as to attach the first end of the thoraco-lumbar plate 340 or 342 to the first pivot bolt receptor 72, and subsequently removed and attached to second pivot bolt receptor 284 so as to be secured to the second end 272 of the thoraco-lumbar plate. Alternatively, a pair of jigs 234 may be used for the attachment of the plate 340 or 342.

The method and operation of use of the thoraco-lumbar plate 340, 342 will now be described. Thoraco-lumbar plate 340 or 342 may be attached to first and second vertebral bodies and third and fourth vertebral bodies using jig 234 as set forth with respect to static and dynamic cervical spine plates 34, 258 and 286. Placement of the thoraco-lumbar plate 340 or 342 varies from the cervical spine plate, in that attachment to the side of the spine occurs. First end portion 264 may be attached to first and second vertebral bodies, followed by attachment of the second end portion 272 to third and fourth vertebral bodies. Secondly, if applicable, a graft 260 may be secured to thoraco-lumbar plate 340 or 342 using bone screws 38 which are inserted into bore(s) 372. When dynamic thoraco-lumbar plate 342 is used, telescopic central portion 352 may be telescopically expanded or contracted to accommodate larger or narrower spaces between the first and second vertebral bodies and the third and fourth vertebral bodies and to permit the placement of a graft 260 or implant therebetween. In this case, as with the dynamic cervical spine plate 286, once the thoraco-lumbar plate 342 is telescopically adjusted and subsequently attached to the first and second vertebral bodies and the third and fourth vertebral bodies using the foregoing method, the plate 342 may be compressed. Threaded locking element 326, such as bone screw(s) 38, is then rotationally inserted into tapered threaded bore 372 from outer surface to vertebrate facing surface using a tool, such as a hex key, simultaneously locking the telescoping assembly and inserting the screw 38 into a graft 260 positioned below the curved central portion 344. Locking element 326, while present in the description of the dynamic thoraco-lumbar plate 342, may not be used in some embodiments.

The thoraco-lumbar plate 340 or 342 used in association with the foregoing method increases the strength of attachment of the plate to the vertebral bodies in the thoraco-lumbar position. Furthermore, the dynamic thoraco-lumbar plate 342 is capable of adjustment for variations in spacing between the first and second vertebral bodies and the third and fourth vertebral bodies, providing a dynamic and strong, secure attachment of the plate to the spine.

Although various representative embodiments of this invention have been described above with a certain degree of particularity, those skilled in the art could make numerous alterations to the disclosed embodiments without departing from the spirit or scope of the inventive subject matter set forth in the specification and claims. All directional references (e.g., upper, lower, upward, downward, left, right, leftward, rightward, top, bottom, above, below, vertical, horizontal, clockwise, counterclockwise, x-axis, y-axis, and z-axis) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected) are to be construed broadly and may include intermediate members between a connection of elements and relative movement between elements. As such, joinder references do not necessarily infer that two elements are directly connected and in fixed relation to each other.

In some instances, components are descried with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to preferred embodiments, persons skilled in the art will recognize that changes may be made in form and detail without departing from the spirit and scope of the invention.

What is claimed is:

1. A spine plate for use with a plurality of bone screws to treat a mammalian body having first and second vertebral bodies in a spine, comprising an elongate plate-like member adapted for fastening respectively to the first and second vertebral bodies, the elongate plate-like member having first and second portions and a longitudinal centerline extending between the end portions, the first portion being provided with first, second and third screw holes adapted for receiving respective first, second and third bone screws that attach to the first vertebral body and the second portion being provided with fourth, fifth and sixth screw holes adapted for receiving respective fourth, fifth and six bone screws that attach to the second vertebral body, the first and second screw holes being transversely-aligned in the first portion and the third screw hole being spaced inwardly from the first and second screw holes towards the second portion and having an axis inclined towards the first and second screw holes and the longitudinal centerline at a fixed angle relative to the plate-like member, the fourth and fifth screw holes being transversely-aligned in the second portion and the sixth screw hole being spaced inwardly from the fourth and fifth screw holes towards the first portion and having an axis inclined towards the fourth and fifth screw holes and the longitudinal centerline at a fixed angle relative to the plate-like member whereby the third and sixth screw holes enhance securement of the first and second portions to the respective first and second vertebral bodies when the bone screws are introduced through the screw holes into the vertebral bodies.

2. A spine plate as in claim 1 wherein each of the first and second screw holes is formed in a bushing pivotally carried by the first portion of the plate-like member and each of the fourth and fifth screw holes is formed in a bushing pivotally carried by the second portion of the plate-like member.

3. A spine plate as in claim 2 wherein each of the bushings has an outer wall and is provided with an internally-threaded bore adapted for receiving one of the plurality of bone screws and a slit extending from the bore through the outer wall permitting radial expansion of the bushing, cooperative engaging means carried by the respective portion and the bushing for providing pivotal movement of the bushing within the respective hole about a single pivot axis and restricting such single pivot axis to a plane extending in the respective portion.

4. A spine plate as in claim 3 wherein the pivot axis relating to the bushing of the first screw hole is perpendicular to the pivot axis relating to the bushing of the second screw hole.

5. A spine plate as in claim 1 wherein the third screw hole is spaced relative to the first and second screw holes and the sixth screw hole is spaced relative to the fourth and fifth screw holes so that each of the third and sixth screw holes is disposed between the first and second vertebral bodies when the plate-like member is fastened to the first and second vertebral bodies.

6. A spine plate as in claim 1 wherein the third and sixth screw holes are spaced transversely of each other.

7. A spine plate for use with a plurality of bone screws to treat a spine of a human body having adjacent first and second vertebral bodies separated by a reconstructed region of an at least partially removed vertebral body from adjacent third and fourth vertebral bodies, comprising an elongate plate-like member having a first end portion adapted for fastening to the first and second vertebral bodies, the first end portion having a length sufficient to extend over the first and second vertebral bodies and being provided with first and second sets of longitudinally spaced-apart threaded screw holes for use with bone screws to secure the elongate plate-like member respectively to the first and second vertebral bodies, the second end portion having a length sufficient to extend over the third and fourth vertebral bodies and being provided with third and fourth sets of longitudinally spaced-apart threaded screw holes for use with bone screws to secure the elongate plate-like member respectively to the third and fourth vertebral bodies, the length of the first end portion approximating the length of the second end portion, the elongate plate-like member having a central portion between the first and second end portions, the central portion having a length of at least half the length of each of the first and second end portions so as to be sufficient to span the reconstructed region in the spine, and each of the first, second, third and fourth sets of longitudinally spaced-apart threaded screw holes including first and second threaded bores transversely-aligned in the respective end portion and a third threaded bore having a fixed axis inclined relative to the end portion and being spaced longitudinally of the first and second threaded bores adapted for receiving respective first, second and third bone screws for attachment to the respective vertebral body.

8. A spine plate as in claim 7, wherein the central portion includes an expansion joint that can expand and contract.

9. A spine plate as in claim 8, wherein the expansion joint is lockable.

10. A spine plate as in claim 7, wherein the first end portion is movable longitudinally relative to the second end portion.

11. A spine repair assembly for use with a screw, comprising a spine plate, an annular bushing distinct from the spine plate and having a threaded bore adapted for receiving the screw, the bushing being provided with a slit extending from the bore through the bushing to permit radial expansion of the bushing, the spine plate having a substantially planar portion and being provided with a hole in the portion for receiving the bushing, and a pin and socket pivot mechanism carried by the portion of the spine plate and the bushing for providing pivotal movement of the bushing within the hole about a single pivot axis and restricting such single pivot axis to a plane extending in the portion of the spine plate whereby when the bushing is disposed in the hole of the spine plate and the screw is threaded into the bushing the bushing can be pivoted to a desired position relative to the spine plate and then positionally locked relative to the spine plate by further advancement of the screw through the bushing so as to cause the bushing to radially expand and frictionally lock within the hole of the spine plate.

12. An assembly as in claim 11 wherein the pin and socket mechanism includes at least one pin provided on one of the portion of the spine plate and the bushing and a socket provided on the other of the spine plate and the bushing.

13. An assembly as in claim 12 wherein the at least one pin includes first and second pins extending from the bushing and the portion of the spine plate is provided with the first and second slots.

14. An assembly as in claim 12 wherein the at least one pin includes first and second pins extending from the portion of the spine plate into the hole and the bushing is provided with the first and second slots.

15. A spine plate for use with a plurality of bone screws to treat a mammalian body having first and second vertebral bodies in a spine, comprising an elongate plate-like member having first and second portions adapted for fastening respectively to the first and second vertebral bodies, the first portion being provided with first, second and third screw holes adapted for receiving respective first, second and third bone screws that attach to the first vertebral body and the second portion being provided with fourth, fifth and sixth screw holes adapted for receiving respective fourth, fifth and six bone screws that attach to the second vertebral body, the first and second screw holes being transversely-aligned in the first portion and the third screw hole being spaced longitudinally of the first and second screw holes, the fourth and fifth screw holes being transversely-aligned in the second portion and the sixth screw hole being spaced longitudinally of the fourth and fifth screw holes, the third screw hole having an axis inclined at a fixed angle relative to the plate-like member and the sixth screw hole having an axis inclined at a fixed angle relative to the plate-like member such that the third and sixth screw holes enhance securement of the first and second portions to the respective first and second vertebral bodies when the bone screws are introduced through the screw holes into the vertebral bodies.

16. A spine plate as in claim 15 wherein each of the first and second screw holes is formed in a bushing pivotally carried by the first portion of the plate-like member and each of the fourth and fifth screw holes is formed in a bushing pivotally carried by the second portion of the plate-like member.

17. A spine plate as in claim 16 wherein each of the bushings pivots about a pivot axis extending in a plane of the respective portion.

18. A spine plate as in claim 17 wherein the pivot axis relating to the bushing of the first screw hole is perpendicular to the pivot axis relating to the bushing of the second screw hole.

19. A spine plate as in claim 16 wherein each of the first and second screw holes is formed in a bushing disposed within a hole in the first portion, cooperative engaging means carried by the first portion and the bushing for restricting pivotal movement of the bushing within the hole about a pivot axis extending in a plane of the first portion.

20. A spine plate as in claim 15 wherein the third and sixth screw holes are spaced transversely of each other.

* * * * *